US009251313B2

(12) United States Patent
Ross et al.

(10) Patent No.: US 9,251,313 B2
(45) Date of Patent: Feb. 2, 2016

(54) SYSTEMS AND METHODS FOR VISUALIZING AND MANAGING TELEPRESENCE DEVICES IN HEALTHCARE NETWORKS

(75) Inventors: Scott Ross, Santa Barbara, CA (US); Kelton Temby, Goleta, CA (US); Jonathan Southard, Santa Barbara, CA (US); Dan Habecker, Santa Barbara, CA (US); Michael C. Chan, Santa Barbara, CA (US); Timothy C. Wright, Santa Barbara, CA (US); Charles S. Jordan, Santa Barbara, CA (US); Joshua A. Bouganim, Goleta, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 880 days.

(21) Appl. No.: 13/444,106

(22) Filed: Apr. 11, 2012

(65) Prior Publication Data

US 2013/0271556 A1 Oct. 17, 2013

(51) Int. Cl.
*H04N 7/14* (2006.01)
*G06F 19/00* (2011.01)
(52) U.S. Cl.
CPC ................... *G06F 19/3418* (2013.01)
(58) Field of Classification Search
None
See application file for complete search history.

(56) References Cited

U.S. PATENT DOCUMENTS

| 3,821,995 | A | 7/1974 | Aghnides |
| 4,107,689 | A | 8/1978 | Jellinek |
| 4,213,182 | A | 7/1980 | Eichelberger et al. |
| 4,413,693 | A | 11/1983 | Derby |
| 4,471,354 | A | 9/1984 | Smith |
| 4,519,466 | A | 5/1985 | Shiraishi |
| 4,553,309 | A | 11/1985 | Hess et al. |
| 4,572,594 | A | 2/1986 | Schwartz |
| 4,625,274 | A | 11/1986 | Schroeder |
| 4,638,445 | A | 1/1987 | Mattaboni |

(Continued)

FOREIGN PATENT DOCUMENTS

| AU | 1216200 A | 5/2000 |
| CA | 2289697 | 11/1998 |

(Continued)

OTHER PUBLICATIONS

Appeal from the U.S. District Court for the Central District of California in case No. 11-cv-9185, Judge Percy Anderson, Joint Appendix, vol. I of IV, Jun. 24, 2013, pp. A1-A6357.

(Continued)

*Primary Examiner* — Maria El-Zoobi

(57) ABSTRACT

Disclosed herein are various embodiments of systems and methods for visualizing, analyzing, and managing telepresence devices operating in a telepresence network of healthcare facilities. The visualization and management system for telepresence devices may display a first viewing level that includes a geographical representation of the location of various telepresence devices. A user may selectively view a global view of all telepresence devices, telepresence devices within a particular region, and/or the details of a particular telepresence device. A user may also access a viewing level of a network of healthcare facilities. The user may view, analyze, and/or manage the healthcare network, telepresence device network, individual telepresence devices, connection rules, and/or other aspects of the healthcare network using the geographical visualization and management tool described herein.

45 Claims, 15 Drawing Sheets

(56) References Cited

U.S. PATENT DOCUMENTS

| | | |
|---|---|---|
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | George et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane et al. |
| 5,006,988 A | 4/1991 | Borenstein et al. |
| 5,040,116 A | 8/1991 | Evans, Jr. et al. |
| 5,051,906 A | 9/1991 | Evans, Jr. et al. |
| 5,073,749 A | 12/1991 | Kanayama |
| 5,084,828 A | 1/1992 | Kaufman |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen, III et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin |
| 5,375,195 A | 12/1994 | Johnston |
| 5,400,068 A | 3/1995 | Ishida et al. |
| 5,413,693 A | 5/1995 | Redepenning |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David |
| 5,442,728 A | 8/1995 | Kaufman et al. |
| 5,462,051 A | 10/1995 | Oka |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | DeVault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |

(56) References Cited

U.S. PATENT DOCUMENTS

| | | | |
|---|---|---|---|
| 6,314,631 B1 | 11/2001 | Pryor |
| 6,317,652 B1 | 11/2001 | Osada |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,411,055 B1 | 6/2002 | Fujita et al. |
| 6,430,471 B1 | 8/2002 | Kintou et al. |
| 6,430,475 B2 | 8/2002 | Okamoto |
| 6,438,457 B1 | 8/2002 | Yokoo |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Liff et al. |
| 6,584,376 B1 | 6/2003 | Van |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury et al. |
| 6,691,000 B2 | 2/2004 | Nagai et al. |
| 6,693,585 B1 | 2/2004 | MacLeod |
| 6,710,797 B1 | 3/2004 | McNelley et al. |
| 6,724,823 B2 | 4/2004 | Rovati et al. |
| 6,728,599 B2 | 4/2004 | Wright et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |

(56) References Cited

U.S. PATENT DOCUMENTS

| | | | |
|---|---|---|---|
| 7,206,627 B2 | 4/2007 | Abovitz et al. | |
| 7,215,786 B2 | 5/2007 | Nakadai et al. | |
| 7,219,364 B2 | 5/2007 | Bolle et al. | |
| 7,222,000 B2 | 5/2007 | Wang et al. | |
| 7,227,334 B2 | 6/2007 | Yang et al. | |
| 7,256,708 B2 | 8/2007 | Rosenfeld | |
| 7,262,573 B2 | 8/2007 | Wang et al. | |
| 7,283,153 B2 | 10/2007 | Provost et al. | |
| 7,289,883 B2 | 10/2007 | Wang et al. | |
| 7,292,257 B2 | 11/2007 | Kang et al. | |
| 7,292,912 B2 | 11/2007 | Wang et al. | |
| 7,305,114 B2 | 12/2007 | Wolff et al. | |
| 7,317,685 B1 | 1/2008 | Flott et al. | |
| 7,321,807 B2 | 1/2008 | Laski | |
| 7,332,890 B2 | 2/2008 | Cohen et al. | |
| 7,333,642 B2 | 2/2008 | Green | |
| 7,346,429 B2 | 3/2008 | Goldenberg et al. | |
| 7,352,153 B2 | 4/2008 | Yan | |
| 7,363,121 B1 | 4/2008 | Chen et al. | |
| 7,382,399 B1 | 6/2008 | McCall | |
| 7,386,730 B2 | 6/2008 | Uchikubo | |
| 7,391,432 B2 | 6/2008 | Terada | |
| 7,400,578 B2 | 7/2008 | Guthrie et al. | |
| 7,404,140 B2 | 7/2008 | O'rourke | |
| 7,421,470 B2 | 9/2008 | Ludwig et al. | |
| 7,430,209 B2 | 9/2008 | Porter | |
| 7,432,949 B2 | 10/2008 | Remy et al. | |
| 7,433,921 B2 | 10/2008 | Ludwig et al. | |
| 7,441,953 B2 | 10/2008 | Banks | |
| 7,467,211 B1 | 12/2008 | Herman et al. | |
| 7,483,867 B2 | 1/2009 | Ansari et al. | |
| 7,492,731 B2 | 2/2009 | Hagendorf | |
| 7,510,428 B2 | 3/2009 | Obata et al. | |
| 7,523,069 B1 | 4/2009 | Friedl et al. | |
| 7,525,281 B2 | 4/2009 | Koyanagi et al. | |
| 7,535,486 B2 | 5/2009 | Motomura et al. | |
| 7,557,758 B2 | 7/2009 | Rofougaran | |
| 7,587,260 B2 | 9/2009 | Bruemmer et al. | |
| 7,587,512 B2 | 9/2009 | Ta et al. | |
| 7,590,060 B2 | 9/2009 | Miceli | |
| 7,593,030 B2 | 9/2009 | Wang et al. | |
| 7,599,290 B2 | 10/2009 | Dos Remedios et al. | |
| 7,624,166 B2 | 11/2009 | Foote et al. | |
| 7,630,314 B2 | 12/2009 | Dos Remedios et al. | |
| 7,631,833 B1 | 12/2009 | Ghaleb et al. | |
| 7,643,051 B2 | 1/2010 | Sandberg et al. | |
| 7,647,320 B2 | 1/2010 | Mok et al. | |
| 7,657,560 B1 | 2/2010 | DiRienzo | |
| 7,680,038 B1 | 3/2010 | Gourlay | |
| 7,693,757 B2 | 4/2010 | Zimmerman | |
| 7,698,432 B2 | 4/2010 | Short et al. | |
| 7,703,113 B2 | 4/2010 | Dawson | |
| 7,719,229 B2 | 5/2010 | Kaneko et al. | |
| 7,737,993 B2 | 6/2010 | Kaasila et al. | |
| 7,739,383 B1 | 6/2010 | Short et al. | |
| 7,756,614 B2 | 7/2010 | Jouppi | |
| 7,761,185 B2 | 7/2010 | Wang et al. | |
| 7,769,492 B2 | 8/2010 | Wang et al. | |
| 7,769,705 B1 | 8/2010 | Luechtefeld | |
| 7,774,158 B2 | 8/2010 | Domingues et al. | |
| 7,813,836 B2 | 10/2010 | Wang et al. | |
| 7,831,575 B2 | 11/2010 | Trossell et al. | |
| 7,835,775 B2 | 11/2010 | Sawayama et al. | |
| 7,860,680 B2 | 12/2010 | Arms et al. | |
| 7,861,366 B2 | 1/2011 | Hahm et al. | |
| 7,885,822 B2 | 2/2011 | Akers et al. | |
| 7,890,382 B2 | 2/2011 | Robb et al. | |
| 7,912,583 B2 | 3/2011 | Gutmann et al. | |
| RE42,288 E | 4/2011 | Degioanni | |
| 7,924,323 B2 | 4/2011 | Walker et al. | |
| 7,949,616 B2 | 5/2011 | Levy et al. | |
| 7,956,894 B2 | 6/2011 | Akers et al. | |
| 7,957,837 B2 | 6/2011 | Ziegler et al. | |
| 7,982,763 B2 | 7/2011 | King | |
| 7,982,769 B2 | 7/2011 | Jenkins et al. | |
| 7,987,069 B2 | 7/2011 | Rodgers et al. | |
| 8,077,963 B2 | 12/2011 | Wang et al. | |
| 8,116,910 B2 | 2/2012 | Walters et al. | |
| 8,170,241 B2 | 5/2012 | Roe et al. | |
| 8,179,418 B2 | 5/2012 | Wright et al. | |
| 8,180,486 B2 | 5/2012 | Saito et al. | |
| 8,209,051 B2 | 6/2012 | Wang et al. | |
| 8,212,533 B2 | 7/2012 | Ota | |
| 8,265,793 B2 | 9/2012 | Cross et al. | |
| 8,287,522 B2 | 10/2012 | Moses et al. | |
| 8,292,807 B2 | 10/2012 | Perkins et al. | |
| 8,320,534 B2 | 11/2012 | Kim et al. | |
| 8,340,654 B2 | 12/2012 | Bratton et al. | |
| 8,340,819 B2 | 12/2012 | Mangaser et al. | |
| 8,348,675 B2 | 1/2013 | Dohrmann | |
| 8,374,171 B2 | 2/2013 | Cho et al. | |
| 8,400,491 B1 | 3/2013 | Panpaliya et al. | |
| 8,401,275 B2 | 3/2013 | Wang et al. | |
| 8,423,284 B2 | 4/2013 | O'Shea | |
| 8,451,731 B1 | 5/2013 | Lee et al. | |
| 8,463,435 B2 | 6/2013 | Herzog et al. | |
| 8,489,641 B1 * | 7/2013 | Seefeld et al. | 707/792 |
| 8,503,340 B1 | 8/2013 | Xu | |
| 8,515,577 B2 | 8/2013 | Wang et al. | |
| 8,527,094 B2 | 9/2013 | Kumar et al. | |
| 8,532,860 B2 | 9/2013 | Daly | |
| 8,610,786 B2 | 12/2013 | Ortiz | |
| 8,612,051 B2 | 12/2013 | Norman et al. | |
| 8,639,797 B1 | 1/2014 | Pan et al. | |
| 8,670,017 B2 | 3/2014 | Stuart et al. | |
| 8,726,454 B2 | 5/2014 | Gilbert, Jr. et al. | |
| 8,750,906 B2 * | 6/2014 | Winkler et al. | 455/457 |
| 8,776,043 B1 * | 7/2014 | Thimsen et al. | 717/171 |
| 8,836,751 B2 | 9/2014 | Ballantyne et al. | |
| 8,849,679 B2 | 9/2014 | Wang et al. | |
| 8,849,680 B2 | 9/2014 | Wright et al. | |
| 8,861,750 B2 | 10/2014 | Roe et al. | |
| 8,897,920 B2 | 11/2014 | Wang et al. | |
| 8,902,278 B2 | 12/2014 | Pinter et al. | |
| 2001/0002448 A1 | 5/2001 | Wilson | |
| 2001/0010053 A1 | 7/2001 | Ben-Shachar et al. | |
| 2001/0020200 A1 | 9/2001 | Das et al. | |
| 2001/0034475 A1 | 10/2001 | Flach et al. | |
| 2001/0034544 A1 | 10/2001 | Mo | |
| 2001/0037163 A1 | 11/2001 | Allard | |
| 2001/0048464 A1 | 12/2001 | Barnett | |
| 2001/0051881 A1 | 12/2001 | Filler | |
| 2001/0054071 A1 | 12/2001 | Loeb | |
| 2001/0055373 A1 | 12/2001 | Yamashita | |
| 2002/0015296 A1 | 2/2002 | Howell et al. | |
| 2002/0027597 A1 | 3/2002 | Sachau | |
| 2002/0027652 A1 | 3/2002 | Paromtchik et al. | |
| 2002/0033880 A1 | 3/2002 | Sul et al. | |
| 2002/0038168 A1 | 3/2002 | Kasuga et al. | |
| 2002/0044201 A1 | 4/2002 | Alexander et al. | |
| 2002/0049517 A1 | 4/2002 | Ruffner | |
| 2002/0055917 A1 | 5/2002 | Muraca | |
| 2002/0057279 A1 | 5/2002 | Jouppi | |
| 2002/0058929 A1 | 5/2002 | Green | |
| 2002/0059587 A1 | 5/2002 | Cofano et al. | |
| 2002/0063726 A1 | 5/2002 | Jouppi | |
| 2002/0073429 A1 | 6/2002 | Beane et al. | |
| 2002/0082498 A1 | 6/2002 | Wendt et al. | |
| 2002/0085030 A1 | 7/2002 | Ghani | |
| 2002/0095238 A1 | 7/2002 | Ahlin et al. | |
| 2002/0095239 A1 | 7/2002 | Wallach et al. | |
| 2002/0098879 A1 | 7/2002 | Rheey | |
| 2002/0104094 A1 | 8/2002 | Alexander et al. | |
| 2002/0106998 A1 | 8/2002 | Presley et al. | |
| 2002/0109770 A1 | 8/2002 | Terada | |
| 2002/0109775 A1 | 8/2002 | White et al. | |
| 2002/0111988 A1 | 8/2002 | Sato | |
| 2002/0120362 A1 | 8/2002 | Lathan et al. | |
| 2002/0123941 A1 * | 9/2002 | Donahue et al. | 705/26 |
| 2002/0128985 A1 | 9/2002 | Greenwald | |
| 2002/0130950 A1 | 9/2002 | James et al. | |
| 2002/0133062 A1 | 9/2002 | Arling et al. | |
| 2002/0141595 A1 | 10/2002 | Jouppi | |
| 2002/0143923 A1 | 10/2002 | Alexander | |

(56) References Cited

U.S. PATENT DOCUMENTS

| | | |
|---|---|---|
| 2002/0177925 A1 | 11/2002 | Onishi et al. |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi |
| 2003/0212472 A1 | 11/2003 | McKee |
| 2003/0216833 A1 | 11/2003 | Mukai et al. |
| 2003/0216834 A1 | 11/2003 | Allard |
| 2003/0220541 A1 | 11/2003 | Salisbury et al. |
| 2003/0220715 A1 | 11/2003 | Kneifel, II et al. |
| 2003/0231244 A1 | 12/2003 | Bonilla et al. |
| 2003/0232649 A1 | 12/2003 | Gizis |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley, Jr. et al. |
| 2004/0010344 A1 | 1/2004 | Hiratsuka et al. |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim, II |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0240981 A1 | 12/2004 | Dothan et al. |
| 2004/0241981 A1 | 12/2004 | Doris et al. |
| 2004/0243712 A1* | 12/2004 | Sakai et al. .................. 709/227 |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0264649 A1 | 12/2005 | Chang et al. |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |

(56) References Cited

U.S. PATENT DOCUMENTS

| | | |
|---|---|---|
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek, Jr. et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0238379 A1* | 10/2006 | Kimchi et al. ............. 340/995.1 |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandbeg et al. |
| 2007/0078566 A1 | 4/2007 | Wang et al. |
| 2007/0093279 A1 | 4/2007 | Janik |
| 2007/0112700 A1 | 5/2007 | Den et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |
| 2010/0268383 A1 | 10/2010 | Wang et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |

(56) References Cited

U.S. PATENT DOCUMENTS

| | | |
|---|---|---|
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0245973 A1 | 10/2011 | Wang et al. |
| 2011/0280551 A1 | 11/2011 | Sammon |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0291809 A1 | 11/2012 | Kuhe et al. |
| 2013/0250938 A1 | 9/2013 | Anandakumar et al. |
| 2013/0321257 A1* | 12/2013 | Moore et al. ............ 345/156 |
| 2014/0032244 A1* | 1/2014 | Kolls et al. .................. 705/3 |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |
| 2014/0250191 A1* | 9/2014 | Altman et al. ............ 709/204 |
| 2015/0053689 A1 | 2/2015 | Chhina |

FOREIGN PATENT DOCUMENTS

| | | |
|---|---|---|
| CN | 1404695 A | 3/2003 |
| CN | 1554193 | 12/2004 |
| CN | 1554985 | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 | 2/2011 |
| CN | 102203759 | 9/2011 |
| CN | 101106939 B | 11/2011 |
| EP | 466492 A2 | 1/1992 |
| EP | 488673 A2 | 6/1992 |
| EP | 0981905 B1 | 2/2002 |
| EP | 1262142 A2 | 12/2002 |
| EP | 1304872 A1 | 4/2003 |
| EP | 1536660 A3 | 9/2004 |
| EP | 1536660 A2 | 6/2005 |
| EP | 1573406 A2 | 9/2005 |
| EP | 1594660 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 | 12/2010 |
| EP | 2300930 | 3/2011 |
| EP | 2342651 | 7/2011 |
| GB | 2431261 A | 4/2007 |
| JP | 07-194609 A | 8/1995 |
| JP | 07213753 | 8/1995 |
| JP | 07248823 A | 9/1995 |
| JP | 07257422 A | 10/1995 |
| JP | 08084328 A | 3/1996 |
| JP | 08320727 A | 12/1996 |
| JP | 09267276 A | 10/1997 |
| JP | 10079097 A | 3/1998 |
| JP | 10288689 A | 10/1998 |
| JP | 11-220706 A | 8/1999 |
| JP | 00032319 A | 1/2000 |
| JP | 00049800 A | 2/2000 |
| JP | 00079587 A | 3/2000 |
| JP | 00196876 A | 7/2000 |
| JP | 00188124 A | 4/2001 |
| JP | 01125641 A | 5/2001 |
| JP | 01147718 A | 5/2001 |
| JP | 01179663 A | 7/2001 |
| JP | 01198865 A | 7/2001 |
| JP | 01198868 A | 7/2001 |
| JP | 01199356 A | 7/2001 |
| JP | 02000574 A | 1/2002 |
| JP | 00235423 A | 2/2002 |
| JP | 02046088 A | 2/2002 |
| JP | 2002101333 A | 4/2002 |
| JP | 2002112970 A | 4/2002 |
| JP | 02305743 A | 10/2002 |
| JP | 2002-321180 A | 11/2002 |
| JP | 02355779 A | 12/2002 |
| JP | 2004-181229 A | 7/2004 |
| JP | 04524824 T | 8/2004 |
| JP | 04261941 A | 9/2004 |
| JP | 2004289379 A | 10/2004 |
| JP | 05028066 A | 2/2005 |
| JP | 2005059170 A | 3/2005 |
| JP | 2005-111083 A | 4/2005 |
| JP | 2006508806 A | 3/2006 |
| JP | 2006109094 A | 4/2006 |
| JP | 2006224294 A | 8/2006 |
| JP | 2006246438 A | 9/2006 |
| JP | 2007007040 A | 1/2007 |
| JP | 2007081646 A | 3/2007 |
| JP | 2007232208 A | 9/2007 |
| JP | 2007316966 A | 12/2007 |
| JP | 2009-125133 A | 6/2009 |
| JP | 10064154 A | 3/2010 |
| JP | 10532109 A | 9/2010 |
| JP | 10246954 A | 11/2010 |
| JP | 2010246954 A | 11/2010 |
| KR | 060037979 | 5/2006 |
| KR | 10-2009-0012542 A | 2/2009 |
| KR | 100019479 A | 2/2010 |
| KR | 100139037 | 12/2010 |
| WO | 93/06690 A1 | 4/1993 |
| WO | 97/42761 A1 | 11/1997 |
| WO | 98/51078 A1 | 11/1998 |
| WO | 99/67067 | 12/1999 |
| WO | 00/25516 A1 | 5/2000 |
| WO | 00/33726 | 6/2000 |
| WO | 01/31861 A1 | 5/2001 |
| WO | 03/77745 A1 | 9/2003 |
| WO | 2004/008738 A1 | 1/2004 |
| WO | 2004/012018 A2 | 2/2004 |
| WO | 2004075456 A2 | 9/2004 |
| WO | 2006012797 | 2/2006 |
| WO | 2006/044847 A2 | 4/2006 |
| WO | 2006/078611 | 4/2006 |
| WO | 2007/041295 A2 | 4/2007 |
| WO | 2007041295 A1 | 4/2007 |
| WO | 2007041038 | 6/2007 |
| WO | 2008100272 A2 | 8/2008 |
| WO | 2008100272 A3 | 10/2008 |
| WO | 2009117274 A2 | 9/2009 |
| WO | 2009128997 A1 | 10/2009 |
| WO | 2009145958 A2 | 12/2009 |
| WO | 2010006205 A1 | 1/2010 |
| WO | 2010006211 A1 | 1/2010 |
| WO | 2010033666 A1 | 3/2010 |
| WO | 2010047881 A1 | 4/2010 |

(56) References Cited

FOREIGN PATENT DOCUMENTS

| | | | |
|---|---|---|---|
| WO | 2010062798 A1 | 6/2010 |
| WO | 2010065257 A1 | 6/2010 |
| WO | 2010120407 A1 | 10/2010 |
| WO | 2011028589 A2 | 3/2011 |
| WO | 2011097130 A3 | 4/2011 |
| WO | 2011097132 A2 | 8/2011 |
| WO | 2011109336 A2 | 9/2011 |
| WO | 2011149902 A2 | 12/2011 |

OTHER PUBLICATIONS

Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.
Appeal from the U.S. District Court for the Central District of California in case No. 11-cv-9185, Judge Percy Anderson, Joint Appendix, vol. IV of IV, Jun. 24, 2013, pp. A15677-A18127.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Civil Minutes-General: Case No. CV 11-9185PA (AJWx), *InTouch Tech., Inc.* v. *VGo Commons, Inc.*, Sep. 10, 2012, 7 pages.
"Magne Charge", Smart Power for Electric Vehicles, Serial No. 75189637, Registration No. 2114006 Filing Date: Oct. 29, 1996, Aug. 26, 1997, 2 pages.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
"PictureTel Adds New Features and Functionality to its Award-Winning Live200 Desktop Videoconferencing System", PR Newswire Association, LLC, Gale, Cengage Learning, Jun. 13, 1997, 5 pages.
Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.
"Using your Infrared Cell Phone Camera", Available on <http://www.catsdomain.com/xray/about.htm>, retrieved on Jan. 23, 2014, Courtesy of Internet Wayback Machine, Jan. 30, 2010, 4 pages.
Office Action received for Chinese Patent Application No. 200680044698.0 on Nov. 4, 2010. (9 pages and 17 pages of English Translation).
Activemedia, Inc., "Saphira Software Manual", Saphira Version 5.3, 1997, 105 pages.
Activmedia Robotics LLC, "Pioneer 2/PeopleBotTM", Operations Manual, Version 9, Oct. 2001, 78 pages.
Apple Inc., "I Phone", iPhone Series, XP002696350, Sep. 21, 2012, pp. 1-29.
Blaer et al., "TopBot: Automated Network Topology Detection With a Mobile Robot", IEEE, Proceedings of the 2003 International Conference on Robotics 7 Automation, Taipei, Taiwan, Sep. 14-19, 2003, pp. 1582-1587.
Bradner, S., "The Internet Standards Process—Revision 3", Network Working Group, Request for Comments: 2026, BCP: 9, Obsoletes: 1602, Category: Best Current Practice, Oct. 1996, pp. 1-36.
Brooks, Rodney A., "A Robust Layered Control System for a Mobile Robot", IEEE, Journal of Robotics and Automation, vol. 2, No. 1, Mar. 1986, pp. 14-23.
Christensen et al., "BeeSoft User's Guide and Reference", Robots for the Real World™, Real World Interface, Inc., Sep. 26, 1997, 203 pages.
Chu et al., "Detection of Target Mobile Signal Strength", Technical Development, Motorola Inc., Jan. 1999, pp. 205-206.

Dario et al., "A Robot Workstation for Diagnosis and Physical Therapy", IEEE Catalog No. 88TH0234-5, Centro "E. Piaggio" University of Pisa, Italy, 1989, pp. 67-72.
Davis, Erik, "Telefriend, Meet iRobot, The Smartest Webcam on Wheels", Wired Magazine, Issue 8.09, available online at <http://www.wired.com/wired/archive/8.09/irobot.html?pg=1&topic=&topic_set=>, retrieved on Jul. 7, 2012, Sep. 2000, 3 pages.
Dean et al., "1992 AAAI Robot Exhibition and Competition", Articles, AI Magazine, vol. 14, No. 1, 1993, 15 pages.
Gaidioz et al., "Synchronizing Network Probes to Avoid Measurement Intrusiveness with the Network Weather Service", High-Performance Distributed Computing, Proceedings of the Ninth International Symposium, 2000, pp. 147-154.
Garner et al., "The Application of Telepresence in Medicine", BT Technology Journal, vol. 15, No. 4, Oct. 1, 1997, pp. 181-187.
Jacobs et al., "Applying Telemedicine to Outpatient Physical Therapy", AMIA, Annual Symposium Proceedings, 2002, 1 page.
Knight et al., "Active Visual Alignment of a Mobile Stereo Camera Platform", Robotics and Automation, Proceedings of ICRA '00, IEEE International Conference, vol. 4, Apr. 24-28, 2000, pp. 3203-3208.
Kurlowicz et al., "The Mini Mental State Examination (MMSE)", Journal of Psychiatric Research, vol. 12, No. 3, 1975, pp. 189-198.
Leifer et al., "VIPRR: A Virtually in Person Rehabilitation Robot", Proceedings of 1997 International Conference on Rehabilitation Robotics, Apr. 14-15, 1997, 4 pages.
Lemaire, Edward, "Using Communication Technology to Enhance Rehabilitation Services", Terry Fox Mobile Clinic, The Rehabilitation Centre, Ottawa, Canada, 2001, 96 pages.
Adams, Chris, "Simulation of Adaptive Behavior (SAB'02)", Mobile Robotics Research Group, The Seventh International Conference, Aug. 4-11, 2002, retrieved on Jan. 22, 2014, available at: http://www.dai.ed.ac.uk/groups/mrg/MRG.html, 1 page.
Minsky, Marvin, "Telepresence", OMNI Magazine, Jun. 1980, 6 pages.
Nakazato et al., "Group-Based Interface for Content-Based Image Retrieval", Proceedings of the Working Conference on Advanced Visual Interfaces, 2002, pp. 187-194.
Nakazato et al., "ImageGrouper: A Group-Oriented User Interface for Content-Based Image Retrieval and Digital Image Arrangement", Journal of Visual Languages and Computing, vol. 14, No. 4, Aug. 2003, pp. 363-386.
Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.
North, Michael, "Telemedicine: Sample Script and Specifications for a Demonstration of Simple Medical Diagnosis and Treatment Using Live Two-Way Video on a Computer Network", Greenstar Corporation, 1998, 5 pages.
Piquepaille, Roland, "This Blog and its RSS Feed are Moving", Roland Piquepaille's Technology Trends, How New Technologies are Modifying our Way of Life, Oct. 31, 2004, 2 pages.
Radvision, "Making Sense of Bandwidth the NetsenseWay", Network Congestion in Unmanaged Networks Bandwidth Estimation and Adaptation Techniques, Radvision's Netsense Technology, 2010, 7 pages.
Reynolds et al., "Review of Robotic Telemedicine Utilization in Intensive Care Units (ICUs)", 11th Annual ATA Symposium, Tampa, Florida, 2011, 1 page.
Roy et al., "Towards Personal Service Robots for the Elderly", Workshop on Interactive Robots and Entertainment (WIRE 2000), vol. 25, Apr. 30-May 1, 2000, 7 pages.
Telepresence Research, Inc., "Telepresence Mobile Robot System", available online at <http://www.telepresence.com/telepresence-research/TELEROBOT/>, retrieved on Nov. 23, 2010, Feb. 20, 1995, 3 pages.
Theodosiou et al., "MuLVAT: A Video Annotation Tool Based on XML-Dictionaries and Shot Clustering", 19th International Conference, Artificial Neural Networks-ICANN, Sep. 14-17, 2009, pp. 913-922.

(56) References Cited

OTHER PUBLICATIONS

Time, Lists, "Office Coworker Robot", Best Inventions of 2001, Available online at <http://content.time.com/time/specials/packages/article/0,28804,1936165_1936255_1936640,00.html>, Nov. 19, 2001, 2 pages.

Tipsuwan et al., "Gain Adaptation of Networked Mobile Robot to Compensate QoS Deterioration", vol. 4, 28th Annual Conference of the Industrial Electronics Society, Nov. 5-8, 2002, pp. 3146-3151.

Tsui et al., "Exploring Use Cases for Telepresence Robots", 6th ACM/IEEE International Conference on Human-Robot Interaction (HRI), Mar. 2011, pp. 11-18.

Tyrrell et al., "Teleconsultation in Psychology: The Use of Videolinks for Interviewing and Assessing Elderly Patients", Age and Ageing, vol. 30 No. 3, May 2001, pp. 191-195.

UMASS Lowell Robotics Lab, "Robotics Lab @ UMASS Lowell", Brochure, 2011, 2 pages.

Weaver et al., "Monitoring and Controling Using the Internet and Java", Proceedings of the 25th Annual Conference of the IEEE Industrial Electronics Society, vol. 3, 1999, pp. 1152-1158.

Weiss et al., "Pebbles: A Personal Technology for Meeting Education, Social and Emotional Needs of Hospitalised Children", Personal and Ubiquitous Computing, vol. 5, No. 3, Aug. 2001, pp. 157-168.

"Appeal from the U.S. District Court for the Central District of California in No. 11-CV-9185, Judge Percy Anderson", May 9, 2014, pp. 1-48.

"Google translation of: Innovations Report", From research project to television star: Care-O-bot in ZDF series, available online at <http://www.innovations-report.de/specials/printa.php?id=5157>, Sep. 28, 2001.

"MPEG File Format Summary", downloaded from: <http://www.fileformat.info/format/mpeg/egff.htm>, Feb. 1, 2001, 8 pages.

"MPEG-4: a Powerful Standard for Use in Web and Television Environments", by Rob Koenen (KPN Research), downloaded from <http://www.w3.org/Architecture/1998/06/Workshop/paper26>, Jul. 1, 1998, 4 pages.

CMU Course 16X62, "Robot user's manual", (describing the Nomad Scout), Carnegie Mellon University, Feb. 1, 2001, 11 pages.

Panusopone et al., "Performance comparison of MPEG-4 and H.263+ for streaming video applications", Circuits Systems Signal Processing, vol. 20, No. 3, 2001, pp. 293-309.

Schraft et al., "Care-O-botTM: The Concept of a System for Assisting Elderly or Disabled Persons in Home Environments", IEEE Proceedings of the 24th Annual Conference of the Industrial Electronics Society, IECON '98, Aug. 31-Sep. 4, 1998, pp. 2476-2481.

Adams, Chris, "Mobile Robotics Research Group", Mobile Robotics Research Group, Edinburgh University, http://www.dai.ed.ac.uk/groups/mrg/MRG.html, Internet, Edinburgh. duplicate of 575084, 2000, pp. 1-2.

Ando, et al., "A Multimedia Self-service Terminal with Conferencing Functions", IEEE, Jul. 5-7, 1995, pp. 357-362.

Android Amusement Corp., "What Marketing Secret . . . Renting Robots from Android Amusement Corp!", (Advertisement), 1982.

Applebome, "Planning Domesticated Robots for Tomorrow's Household", New York Times, http://www.theoldrobots.com/images17/dc17.JPG, Mar. 4, 1982, pp. 21, 23.

Baltus, et al., "Towards Personal Service Robots for the Elderly, Proceedings for the Elderly Workshop on Interactive Robots and Entertainment", Computer Science and Robotics, 2000.

Bar-Cohen, et al., "Virtual reality robotic telesurgery simulations using MEMICA haptic system", Internet, Mar. 5, 2001, pp. 1-7.

Barrett, "Video Conferencing Business Soars as Companies Cut Travel; Some Travel Cuts Are Permanent", http://www.ivci.com/international_videoconferencing_news_videoconferencing_news_19.html, May 13, 2002.

Bauer, Jeffrey C. et al., "Service Robots in Health Care: The Evolution of Mechanical Solutions to Human Resource Problems", Jun. 2003.

Bischoff, "Design Concept and Realization of the Humanoid Service Robot Hermes", Field and Service Robotics, Springer, London, 1998, pp. 485-492.

Blackwell, Gerry, "Video: A Wireless LAN Killer App?", Internet, Apr. 16, 2002, pp. 1-3.

Breslow, Michael J. et al., "Effect of a multiple-site intensive care unit telemedicine program on clinical and economic outcome an alternative paradigm for intensivist staffing", Critical Care Med; vol. 32 No. 1, Jan. 2004, pp. 31-38.

Brooks, Rodney, "Remote Presence", Abstracts from Flesh & Machines, How Robots Will Change Us, Feb. 2002, pp. 131-147.

Candelas, Herias et al., "Flexible virtual and remote laboratory for teaching Robotics", FORMATEX 2006; Proc. Advance in Control Education Madrid, Spain, Jun. 2006, pp. 21-23.

Celi, et al., "The EICU: It's not just telemedicine", Critical Care Medicine vol. 29, No. 8 (Supplement), Aug. 2001.

Cheetham, Anastasia et al., "Interface Development for a Child's Video Conferencing Robot", 2000, pp. 1-4.

Cleary, et al., "State of the art in surgical robotics: Clinical applications and technology challenges", Internet, Feb. 24, 2002, pp. 1-26.

CNN, "Floating 'droids' to roam space corridors of the future", Internet, Jan. 12, 2000, pp. 1-4.

cnn.com/technology, "Paging R.Robot: Machine helps doctors with patients", Internet, Sep. 30, 2003, 1-3.

Crowley, Susan L., "Hello to Our Future", AARP Bulletin, http://www.cs.cmu.ed/-nursebot/web/press/aarp 99_14/millennium.html, Jan. 2000.

Dalton, "Techniques for Web Telerobotics", PhD Thesis, University of Western Australia, http://telerobot.mech.uwa.edu.au/information.html, http://catalogue.library.uwa.edu.au/search, 2001, 27-62 pp. 149-191.

Davies, "Robotics in Minimally Invasive Surgery", Internet, 1995, pp. 5/1-5/2.

Defendant VGo Communications, Inc.'s Invalidity Contentions Pursuant to the Feb. 27, 2012 Civil Minute Order, May 2, 2012.

Defendant-Counterclaimant VGo Communications, Inc.'s Supplemental Invalidity Contentions Pursuant to the Feb. 27, 2012 Civil Minute Order, May 14, 2012.

Digiorgio, James, "Is Your Emergency Department of the 'Leading Edge?", Internet, 2005, pp. 1-4.

Discovery Channel Canada, "Inventing the Future: 2000 Years of Discovery", (Video Transcript), Jan. 2, 2000.

Dudenhoeffer, et al., "Command and Control Architectures for Autonomous Micro-Robotic Forces", http://www.inl.gov/technicalpublications/Documents/3157051.pdf, Apr. 2001.

Elhajj, "Real-Time Haptic Feedback in Internet-Based Telerobotic Operation", IEEE International Conference on Electro/Information Technology, Jun. 2000 http://www.egr.msu.edu/~ralab-web/cgi_bin/internet-teleoperation.php.

Elhajj, et al., "Supermedia in Internet-based telerobotic operations", Internet, 2001, pp. 1-14.

Elhajj, et al., "Synchronization and Control of Supermedia Transmission Via the Internet", Proceedings of 2001 International Symposium on Intelligent Multimedia Video and Speech Processing., Hong Kong, May 2-4, 2001.

Fels, "Developing a Video-Mediated Communication System for Hospitalized Children", Telemedicine Journal, vol. 5,vol. 5, No. 2, 1999.

Fetterman, "Videoconferencing over the Internet", Internet, 2001, pp. 1-8.

Fiorini, P., et al, "Health Care Robotics: A Progress Report", IEEE International Conference on Robotics and Automation, Apr. 1997, pp. 1271-1276.

Fong, "Collaborative Control: A Robot-Centric Model for Vehicle Teleoperation", The Robotics Institute Carnegie Mellon University, Nov. 2001 http://web.archive.org/web/20030504040803/www.ricmu.edu/cgi-bin/tech_reports.cgi?year=2001&text=0.

Ghiasi, et al., "A Generic Web-based Teleoperations Architecture: Details and Experience", SPIE Conference on Telemanipulator and Telepresence Technologies VI, Sep. 1999.

Goldberg, et al., "Collaborative Teleoperation via the Internet", IEEE International Conference on Robotics and Automation, San Francisco, California, Apr. 2000.

(56) References Cited

OTHER PUBLICATIONS

Goldberg, "Desktop Teleoperation via the World Wide Web, Proceedings of the IEEE International Conference on Robotics and Automation", htto://citeseer.ist.osu.edu/cache/oaoers/cs/5/fto:zSzzSzusc.eduzSzoubzSziriszS zraiders.odf/aol, 1995, pp. 654-659.

Goldberg, "More Online Robots, Robots that Manipulate", Internet, Updated Aug. 2001, http://ford.ieor.berkeley.edu/ir/robots_a2.html, Aug. 2001.

Goldenberg, et al., "Telemedicine in Otolaryngology", American Journal of Otolaryngology vol. 23, No. 1, 2002, pp. 35-43.

Goldman, Lea, "Machine Dreams", Entrepreneurs, Forbes, May 27, 2002.

Gump, Michael D., "Robot Technology Improves VA Pharmacies", Internet, 2001, pp. 1-3.

Hameed, Mohammed et al., "A Review of Telemedicine", Journal of Telemedicine and Telecare., vol. 5, Supplement 1, 1999, pp. S1:103-S1:106.

Han, et al., "Construction of an Omnidirectional Mobile Robot Platform Based on Active Dual-Wheel Caster Mechanisms and Development of a Control Simulator", Kluwer Acedemic Publishers, vol. 29, Nov. 2000, pp. 257-275.

Handley, et al., "RFC 2327—SDP:Session Description Protocol", http://www.faqs.org/rfcs/rfc2327.html, Apr. 1998.

Hanebeck, et al., "ROMAN: A mobile Robotic Assistant for Indoor Service Applications", Proceedings of the 1997 IEEE/RSJ International Conference on Intelligent Robots and Systems, 1997.

Harmo, et al., "Moving Eye-Interactive Telepresence Over Internet With a Ball Shaped Mobile Robot", 2000.

Haule, et al., "Control Scheme for Delayed Teleoperation Tasks", Proceedings of the Pacific Rim Conference on Communications, Computer and Signal Processing, May 17, 1995.

Hees, William P., "Communications Design for a Remote Presence Robot", Jan. 14, 2002.

Holmberg, "Development of a Holonomic Mobile Robot for Mobile Manipulation Tasks", International Conference on Field and Service Robotics, Pittsburgh, PA, Aug. 1999.

Ishiguro, "Integrating a Perceptual Information Infrastructure with Robotic Avatars: A Framework for Tele-Existence", Proceeding of IEEE Conference on Intelligent Robots and Systems, 1999, pp. 1032-1038.

Ishihara, et al., "Intelligent Microbot DDS (Drug Delivery System) Measured and Controlled by Ultrasonics", IEEE/RSJ, vol. 2, Nov. 3-5, 1991, pp. 1145-115.

ITU, "ITU-T H.281 A Far End Camera Control Protocol for Videoconferences using H.224", http://www.itu.int/rec/T-RECH.281-199411-I/en, Nov. 1994.

ITU, "ITU-T H.323 Packet-based multimedia communications", http://www.itu.int/rec/T-REC-H.323-199802-S/en, Feb. 1998.

ITU, "ITU-T H.450.9 Call Completion Supplementary Services for H.323", http://www.itu.int/rec/T-RECH.450.9-200011-I/en, Nov. 2000.

ITU, "ITU-T H.450.11 Call Intrusion Supplementary Service for H.323", http://www.itu.int/rec/T-RECH.450.11-200103-I/en, Mar. 2001.

Ivanova, Natali, "Master's thesis: Internet Based Interface for Control of a Mobile Robot", Department of Numerical Analysis and Computer Science, 2003, 59 pages.

Jenkins, et al., "Telehealth Advancing Nursing Practice", Nursing Outlook, vol. 49, No. 2, Mar./Apr. 2001.

Johanson, "Supporting video-mediated communication over the Internet", Chalmers University of Technology,Dept of Computer Engineering, Gothenburg, Sweden, 2003.

Jouppi, et al., "Mutually-Immersive Audio Telepresence", Audio Engineering Society Convention Paper presented at 113th Convention, Oct. 2002.

Jouppi, Norman et al., "First Steps Towards Mutually-Immersive Mobile Telepresence", CSCW, 02, New Orleans LA, Nov. 16-20, 2002.

Kanehiro, Fumio et al., "Virtual Humanoid Robot Platform to Develop Controllers of Real Humanoid Robots without Porting", IEEE, 2001, pp. 3217-3276.

Keller, et al., "Raven Interface Project", http://upclose.Irdc.pitt.edu/people.Iouw_assets/Raven_Slides.pps, Fall 2001.

Khatib, "Robots in Human Environments", Proc. International Conference on Control, Automation, Robotics, and Vision ICRACV2000, Singapore, Dec. 2000, pp. 454-457.

Kuzuoka, et al., "Can the GestureCam Be a Surrogate?", Proceedings of the Fourth European Conference on Computer-Supported Cooperative Work, Sep. 10-14, pp. 181-196.

Lane, "Automated Aides", Newsday, http://www.cs.cum.edu/nursebot/web/press/nd4380.htm, Oct. 17, 2000.

Lee, et al., "A novel method of surgical instruction: International telementoring", Internet, 1998, pp. 1-4

Lim, Hun-Ok et al., "Control to Realize Human-like Walking of a Biped Humanoid Robot", IEEE, 2000, pp. 3271-3276.

Linebarger, John M. et al., "Concurrency Control Mechanisms for Closely Coupled Collaboration in Multithreaded Virtual Environments", Presence, Special Issue on Advances in Collaborative VEs, 2004.

Loeb, et al., "Virtual Visit: Improving Communication for Those Who Need It Most", Stud Health Technol Inform.; 94: 2003 pp. 302-308.

Long, "HelpMate Robotics, Inc. (Formerly Transitions Research Corporation) Robot Navigation Technology", NIST Special Publication, http://www.atp.nist.gov/eao/sp950-1/helpmate.htm, Mar. 1999, pp. 950-951.

Luna, Nancy, "Robot a new face on geriatric care", OC Register, Aug. 6, 2003.

Mack, "Minimally invasive and robotic surgery", Internet IEEE, 2001, pp. 568-572.

Mair, "Telepresence—The Technology. And Its Economic and Social Implications", IEEE Technology and Society, 1997.

Martin, Anya, "Days Ahead", Assisted Living Today, vol. 9, Nov./Dec. 2002, pp. 19-22.

McCardle, et al., "The challenge of utilizing new technology in design education", Internet, 2000, pp. 122-127.

Meng, et al., "E-Service Robot in Home Healthcare", Proceedings of the 2000 IEEE/RSJ, International Conference on Intelligent Robots and Systems, 2000, pp. 832-837.

Metz, "HP Labs", PCMAG.com, http://www.pcmag.com/article2/0,2817, 1130820,00.asp, Jul. 1, 2003.

Michaud, "Introducing Nursebot", The Boston Globe, http://www.cs.cmu.edu/nursebot/web/press/globe 3 01/index.html, Sep. 11, 2001, pp. 1-5.

Montemerlo, "Telepresence: Experiments in Next Generation Internet", CMU Robotics Institute, http://www.ri.cmu.edu/creative/archives.htm (Video/Transcript), Oct. 20, 1998.

Murphy, "Introduction to A1 Robotics", A Bradford Book, 2000, p. 487.

Nakajima, et al., "A Multimedia Teleteaching System using an Electronic Whiteboard for Two Way Communication of Motion Videos and Chalkboards", IEEE, 1993, pp. 436-441.

Nomadic Technologies Inc., "Nomad XR4000 Hardware Manual", Release 1.0, Mar. 1999.

Nt'l Energy Res Sci Comp Ctr, "Berkeley Lab's Rage Telepresence Robot Captures R&D100 Award", http://www.nersc.gov/news/newsroom/RAGE070202.php, Jul. 2, 2002.

Ogata, et al., "Development of Emotional Communication Robot: WAMOEBA-2r- Experimental evaluation.", IEEE, 2000, pp. 175-180.

Ogata, et al., "Emotional Communication Robot: WAMOEBA-2R—Emotion Model and Evaluation Experiments", Internet, 1999, pp. 1-16.

Oh, et al., "Autonomous Battery Recharging for Indoor Mobile Robots", Proceedings of Australian Conference on Robotics and Automation, http://users.rsise.anu.edu.au/rsl/rsl_papers/ACRA2000/Auto_Recharge_Paper. pdf, 2000.

Ojha, A. K., "An application of Virtual Reality in Rehabilitation", IEEE, Apr. 10-13, 1994, pp. 4-6.

Paulos, et al., "A World Wide Web Telerobotic Remote Environment Browser", http://vive.cs.berkeley.edu/capek, 1995.

(56) References Cited

OTHER PUBLICATIONS

Paulos, "Designing Personal Tele-embodiment", IEEE International Conference on Robotics and Automation http://www.prop.org/papers/icra98.pdf, 1998.
Paulos, "PRoP: Personal Roving Presence", ACM:CHI Proceedings of CHI '98, http://www.prop.org/papers/chi98.pdf, 1998, p. 6.
Paulos, et al., "Ubiquitous Tele-embodiment: Applications and Implications", International Journal of Human Computer Studies, vol. 46, No. 6, Jun. 1997, pp. 861-877.
Paulos, "Video of PRoP 2 at Richmond Field Station", www.prop.org Printout of Home Page of Website and two-page Transcript of the audio portion of said PRoP Video, May 2001.
Paulos, Eric J., "Personal Tele-Embodiment", UC Berkeley, Fall 2001.
Picturetel, PictureTel Live200 for Windows NT Product Guide, http://support.polycom.com/global/documents/support/user/products/video/live200_live200NT_product_guide.pdf, Nov. 1994.
Pin, et al., "A New Family of Omnidirectional and Holonomic Wheeled Platforms for Mobile Robots", IEEE, vol. 10, No. 4, Aug. 1994.
Roach, "Automatic Call Back Service in SIP", http://tools.ietf.org/pdf/draftroach-sip-acb-00.pdf, Mar. 2000.
Rovetta, et al., "A New Telerobotic Application: Remote Laparoscopic Surgery Using Satellites and and optical fiber Networks for Data Exchange", International Journal of Robotics Research, Jun. 1, 1996, pp. 267-279.
Roy, et al., "Towards Personal Service Robots for the Elderly", Internet, Mar. 7, 2002, 7 pgs.
Salemi, et al., "MILO: Personal robot platform", Internet, 2005, pp. 1-6.
Sandt, Frederic et al., "Perceptions for a Transport Robot in Public Environments", IROS, 1997.
Schaeffer, "Care-O-bot: A System for Assisting Elderly or Disabled Persons in Home Environments", Proceedings of AAATE-99, http://morpha.de/download/publications/IPA, 1999.
Schulz, "Web Interfaces for Mobile Robots in Public Places", Robotics & Automation Magazine, IEEE, vol. 7, Issue 1, Mar. 2000.
Shimoga, et al., "Touch and force reflection for telepresence surgery", IEEE, 1994, pp. 1049-1050.
Siegwart, "Interacting Mobile Robots on the Web", Proceedings of the 1999 IEEE International Conference on Robotics and Automation, May 1999.
Simmons, "Xavier: An Autonomous Mobile Robot on the Web", IEEE Robotics and Automation Magazine, 1999, pp. 43-48.
Spawar Systems Center, "Robart", San Diego, CA, http://www.nosc.mil/robots/land/robart/robart.html, 1998, pp. 1-8.
Stephenson, Gary, "Dr. Robot Tested at Hopkins", Internet, Aug. 5, 2003, pp. 1-2.
Stoianovici, et al., "Robotic Tools for Minimally Invasive Urologic Surgery", Internet, Dec. 2002, pp. 1-17.
Summers, "Microsoft NetMeeting 3 Features" excerpt from Official Microsoft NetMeeting 3.0 Book, http://technet.microsoft.com/en-us/library/cc723477.aspx#XSLTsection121121120120, excerpt from Microsoft Press http://www.computerbooksonline.com/abook.asp?i=0735605823, Mar. 1999.
Suplee, "Mastering the Robot", The Washington Post, http://www.cs.cmu.edu-nursebotlweb/press/wash/index.html, Sep. 17, 2000, p. A01.
Tahboub, Karim A. et al., "Dynamics Analysis and Control of a Holonomic Vehicle With Continously Variable Transmission", Journal of Dynamic Systems, Measurement and Control ASME vol. 124, Mar. 2002, pp. 118-126.
Tendick, et al., "Human-Machine Interfaces for Minimally Invasive Surgery", IEEE, 1997, pp. 2771-2776.
Thrun, et al., "Probabilistic Algorithms and the Interactive Museum Tour-Guide Robot Minerva", Internet, 2000, pp. 1-35.
Tzafestas, et al., "VR-based Teleoperation of a Mobile Robotic Assistant: Progress Report", Internet, Nov. 2000, pp. 1-23.
Urquhart, Kim , "InTouch's robotic Companion 'beams up' healthcare experts", Medical Device Daily, vol. 7, No. 39, Feb. 27, 2003, p. 1,4.
West, et al., "Design of Ball Wheel Mechanisms for Omnidirectional Vehicles with Full Mobility and Invariant Kinematics", Journal of Mechanical Design , vol. 119, Jun. 1997, pp. 153-161.
Yamasaki, et al., "Applying Personal Robots and Active Interface to Video Conference Systems", Internet, 1995, pp. 243-248.
Yamauchi, "PackBot: A Versatile Platform for Military Robotics", Internet, 2004, pp. 1-10.
Yong, et al., "Robot task execution with telepresence using virtual reality technology", Internet, 1998, pp. 1-8.
Zambroski, "CMU, Pitt Developing 'nursebot'", http://www.cs.cmu.edu/~nursebot/web/press/tribunereview.html, Oct. 27, 2000.
Zamrazil, Kristie, "Telemedicine in Texas: Public Policy Concerns", House Research Organization Focus Report, Texas House of Representatives, http://www.hro.house.state.tx.us/focus/telemed.pdf, May 5, 2000, pp. 76-22.
Zipperer, Lorri, "Robotic dispensing system", ISMP Medication Safety Alert! vol. 4, Issue 17, Aug. 25, 1999, pp. 1-2.
Zorn, Benjamin G., "Ubiquitous Telepresence", http://www.cs.colorado.edu/-zorn/utlvision/vision.html, May 5, 1996.
Nomadic Technologies, Inc., "Nomad Scout User's Manual", Software Version 2.7, Part No. DOC00004, Jul. 12, 1999, pp. 1-59.
ACM Digital Library Record, Autonomous Robots, vol. 11, No. 1, Table of Content, available at <http://dl.acm.org/citation.cfm?id=591550&picked=prox&cfid=360891374 &cftoken=35225929>, Jul. 2001, 2 pages.
Brenner, Pablo, "A Technical Tutorial on the IEEE 802.11 Protocol", BreezeCOM Wireless Communications, Jul. 18, 1996, pp. 1-24.
Library of Congress, "008-Fixed-Length Data Elements (NR)", MARC 21 Format for Classification Data, available at <http://www.loc.gov/marc/classification/cd008.html>, retrieved on Jul. 22, 2014, pp. 1-14.
Paulos et al., "Personal Tele-Embodiment", Chapter 9 in Goldberg et al., Ed., "Beyond Webcams", MIT Press, Jan. 4, 2002, pp. 155-167.
Paulos et al., "Social Tele-Embodiment: Understanding Presence", Autonomous Robots, vol. 11, No. 1, Kluwer Academic Publishers, Jul. 2001, pp. 87-95.
Paulos, Eric John, "Personal Tele-Embodiment", Introductory and Cover Pages from 2001 Dissertation Including Contents table, together with E-mails Relating thereto from UC Berkeley Libraries, as Shelved at UC Berkeley Engineering Library (Northern Regional Library Facility), May 8, 2002, 25 pages (including 4 pages of e-mails).
Paulos, Eric John, "Personal Tele-Embodiment", OskiCat Catalog Record, UCB Library Catalog, Results page and MARC Display, retrieved on Jun. 14, 2014, 3 Pages.
Screenshot Showing Google Date for Lemaire Telehealth Manual, Screenshot Retrieved on Dec. 18, 2014, 1 page.
Nomadic Technologies, Inc., "Nomad Scout Language Reference Manual", Software Version: 2.7, Part No. DOC00002, Jul. 12, 1999, 47 pages.
Fulbright et al., "SWAMI: An Autonomous Mobile Robot for Inspection of Nuclear Waste of Storage Facilities", Autonomous Robots, vol. 2, 1995, pp. 225-235.

\* cited by examiner

SYSTEMS AND METHODS FOR VISUALIZING AND MANAGING TELEPRESENCE DEVICES IN HEALTHCARE NETWORKS

TECHNICAL FIELD

This disclosure relates to managing telepresence devices in healthcare networks. More specifically, this disclosure provides various visualization and management systems for use with telepresence devices, healthcare networks, and associated information.

BRIEF DESCRIPTION OF THE DRAWINGS

Non-limiting and non-exhaustive embodiments of the disclosure are described herein, including various embodiments of the disclosure illustrated in the figures listed below.

Figure 1:
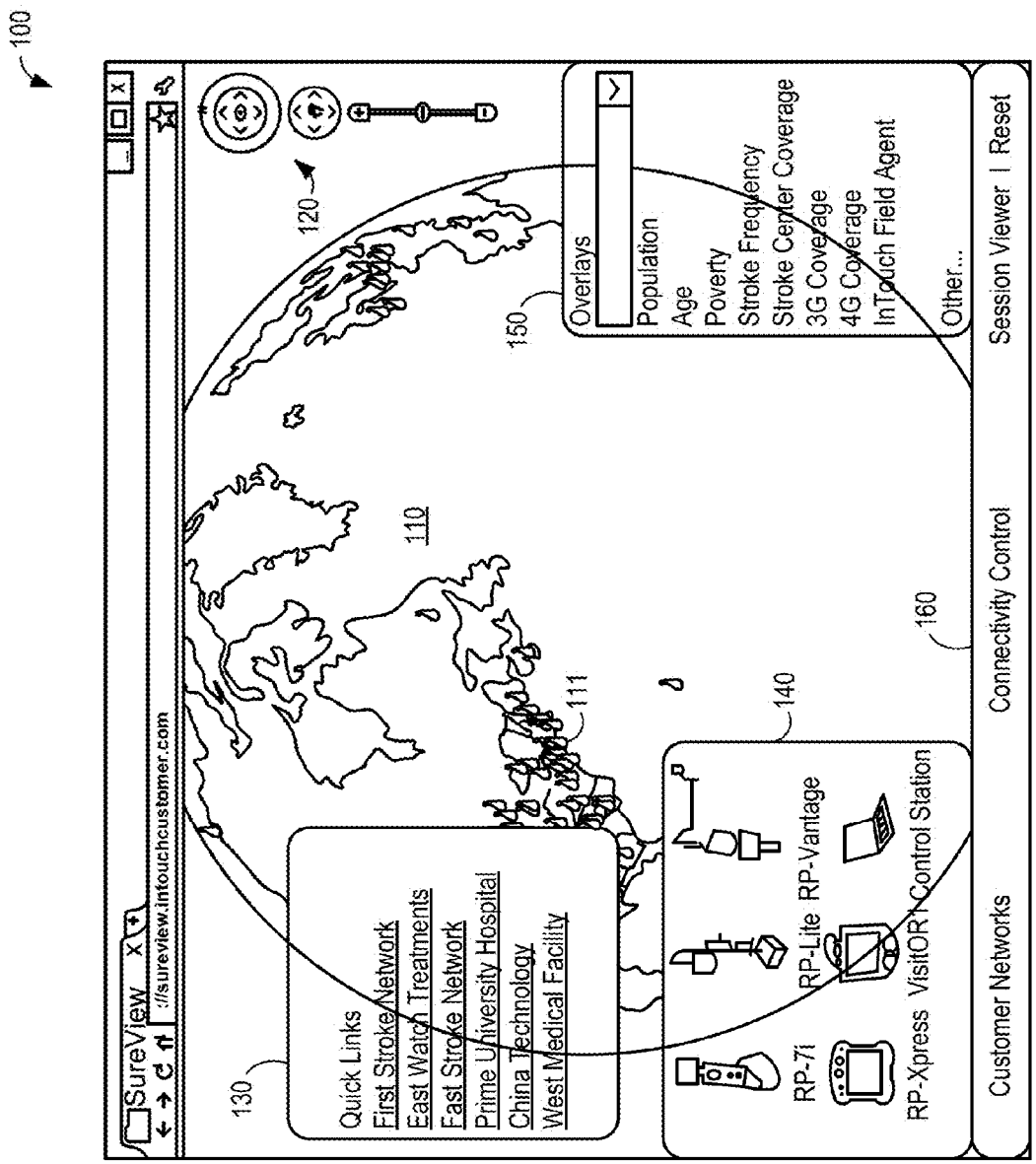
FIG. 1 illustrates a viewing level including a geographical representation of the world, shortcut links to various geographical locations, selectable icons associated with various device types, a navigation input panel, and selectable overlays.

The described features, structures, and/or characteristics of the systems and methods described herein may be combined in any suitable manner in one or more alternative embodiments, and may differ from the illustrated embodiments.

DETAILED DESCRIPTION

The present disclosure provides various systems and methods for visualizing and managing telepresence devices within healthcare networks and facilities. Using the presently described visualization and management tool, users may more efficiently visualize, analyze, and actively manage various aspects of a telepresence healthcare network. In some embodiments, a user may view a geographical representation of the relative location of each of a plurality of telepresence devices in a telepresence network.

Healthcare facilities may include telemedicine technologies, such as telepresence devices in a telepresence network, that allow remote healthcare practitioners to provide services to patients and/or other healthcare practitioners in remote locations. For example, a remote medical professional may be a neurologist practicing in a major hospital who may, via telepresence devices, provide services and consultations to patients and other medical professionals in hospitals located in rural areas that may otherwise not have a neurologist on staff.

The telepresence devices may operate as part of a telepresence network associated with one or more healthcare networks. Each healthcare network may include one or more healthcare facilities (e.g., hospitals, rehabilitation facilities, and long-term care facilities) that each have one or more telepresence devices. Types of telepresence devices include, but are not limited to, remote telepresence devices, mobile telepresence units, and/or control stations. For example, a remote telepresence device may include a telepresence robot configured to move within a medical facility and provide a means for a remote practitioner to perform remote consultations.

A visualization and management system for telepresence devices may be configured to display a first viewing level that includes a geographical representation of the location of various telepresence devices. The viewing level may include all telepresence devices, those within predefined geographical boundaries, those associated with a particular healthcare network, or those associated with a particular healthcare facility. The telepresence devices and/or healthcare facilities may also be displayed as hub devices/facilities and spoke devices/facilities. The various interconnections between the hubs and spokes may be selectively displayed.

A navigation control panel may allow a user to navigate within the geographical representation. For example, the navigation panel may allow for panning, tilting, scrolling, compass alignments, and/or other navigational options. Additionally, the field of view may be dynamically modified based on a user's selection. For example, the field of view may be controlled by a zooming panel or icon, or alternatively may be dynamically adjusted based on other navigational or icon selections. The information associated with the displayed telepresence devices and/or healthcare facilities may be limited or expanded based on the number of telepresence devices and/or healthcare facilities currently displayed in the selected field of view. In some embodiments, shortcuts may allow a user to quickly navigate to a specific geographical location, to a specific medical facility, to a specific medical network, and/or to a specific telepresence device.

The first viewing level may include various icons, panels, buttons, and/or other selectable options configured to allow a user to select one or more alternative viewing levels. For example, a device detail request module may allow a user to submit a detail request in order to view detailed information associated with one or more telepresence devices, healthcare facilities, and/or healthcare practitioners shown on the geographical representation. A user may request additional details by selecting a particular telepresence device and/or healthcare facility. In some embodiments, additional details may be presented when a user mouses over a device/facility. The mouse-over may cause a pop-up overlay to appear displaying additional details associated with the device/facility. The details associated with one or more telepresence devices may include the connection strength, the number of active sessions, a history of technical problems, a history of session activity, shipping information associated with a telepresence device, information associated with a software update, information associated with a firmware update, a serial number, a model number, a battery level, a date the telepresence device last reported, a time the telepresence device last reported, historical session data, a registered peripheral, a licensed application, a total utilization time, an average session duration, a duration of a particular session, a start time of a particular session, an end time of a particular session, a Quality of Service (QoS) for one or more sessions, a current available bandwidth, a bandwidth availability with respect to time, a current location of a telepresence device, and historical locations of a telepresence device with respect to time.

Similarly, the details associated with one or more healthcare facilities may include a number of active sessions, a number of active telepresence devices, a connection strength of telepresence devices, a connection between two or more telepresence devices, a location of a telepresence device, information from a StrokeRESPOND application, a door-to-needle time, a door-to-balloon time, t-PA contraindication and warning information, a healthcare practitioner response time, and a call center response time.

Additionally, details associated with a particular telepresence device, healthcare facility, healthcare network, and/or healthcare practitioner may include one or more connection rules. For example, connection rules may define where, when, and how a healthcare facility, healthcare network, and/or healthcare practitioner may access, view, monitor, and/or control a particular telepresence device or set of telepresence devices. The connection rules may also define who is granted access and what devices they can view. In some embodiments, a viewing level displaying one or more connection rules may allow a user to manage and/or configure the various connection rules between devices, facilities, and/or practitioners. In one embodiment, connection rules may be managed using drag-and-drop actions between devices, facilities, and/or practitioners.

Some of the viewing levels may include geographical representations constrained by particular geographical boundaries, the extent of a healthcare network, or the location of associated telepresence devices. Some of the viewing levels may include selectable overlays configured to overlay information on the geographical representations. Accordingly, a user may apply an informational overlay to a geographical representation that includes various healthcare facilities and/or telepresence devices.

Examples of overlays include, but are not limited to, a population density, a stroke frequency, an adoption rate of a software update, an adoption rate of a firmware update, a frequency of a particular medical condition, a frequency of a particular technical difficulty, an average age of the population, an average age of patients, socioeconomic conditions, an availability of wireless communications, a relative location of medical practitioners, active sessions, a data connection strength, and a relative location of support technicians. The informational overlay may be overlaid on the geographical representation as a heat map, as graphics, as pictures, as icons, as numbers, and/or as text.

In some embodiments, the informational overlay may be overlaid on the entire geographical representation. In other embodiments, the informational overlay may be overlaid on a portion of the geographical representation. For example, the informational overlay may only be overlaid on the portion of a geographical representation that corresponds to a geographical area serviced by a particular healthcare network, hospital, hub hospital, spoke hospital, telepresence device, support technician, and/or medical practitioner.

In some embodiments, a viewing level may include a geographical representation displaying the relative location of various telepresence devices. The viewing level may include various selectable device icons that each correspond to a particular type of telepresence device. The device icons may be used to toggle between displaying and not displaying the associated type of telepresence device. Accordingly, a user may toggle the device icons in order to view all of the control stations, but not the mobile telepresence units or the remote telepresence robots. Within the same viewing level, the user may toggle the device icons to view the remote telepresence robots and/or the mobile telepresence units, but not the control stations. Additional device icons may further differentiate between device types, models, vintages, active telepresence devices, inactive telepresence devices, and/or other characteristics of the various telepresence devices.

The visualization and management of telepresence networks may allow healthcare facilities, healthcare networks, healthcare practitioners, technical support personnel, and/or other users to improve patient care, provide enhanced telepresence services, reduce the costs associated with telepresence consultations, and/or otherwise improve existing technologies and systems. Suitable networks for use with the present visualization and management systems include any of a wide variety of physical infrastructures, protocols, connections, and encryption algorithms. According to various embodiments, networking practices may be implemented in order to comply with accepted healthcare standards and/or government regulations.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. In particular, an "embodiment" may be a system, an article of manufacture (such as a computer-readable storage medium), a method, and/or a product of a process.

The phrases "connected to" and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless otherwise specified.

Embodiments may include various features, which may be embodied in machine-executable instructions executed by a general-purpose or special-purpose computer (or other electronic device). Alternatively, the features may be performed by hardware components that include specific logic for performing the steps or by a combination of hardware, software, and/or firmware. Accordingly, the various components, modules, systems, and/or features described herein may be embodied as modules within a system. Such a system may be implemented in software, firmware, hardware, and/or physical infrastructure.

Embodiments may also be provided as a computer program product including a non-transitory machine-readable medium having stored thereon instructions that may be used to program or executed on a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable media suitable for storing electronic instructions.

FIG. 1 illustrates a global viewing level 100 of a geographical representation of the world 110. As illustrated, the global viewing level 100 may include a navigation panel 120 with various icons configured to allow a user to pan, rotate, tilt, and zoom within the global viewing level. For instance, a slider bar may be slid between a "−" sign and a "+" sign in order to control the field of view of the geographical representation 110. A wide field of view may include the entire globe, as illustrated, and a narrow field of view may be limited to a single telepresence device and/or healthcare facility. The global viewing level 100 may include various quick links 130. A user may use the quick links 130 to navigate to a specific location on the geographical representation 110 and/or automatically adjust the field of view.

The viewing level 100 may also include a panel 140 of device-type icons. By selecting a device icon in the panel 140, a user may choose whether or not the particular device type is displayed on the geographical representation 110. For example, the illustrated viewing level 100 displays icons representing various telepresence devices on the geographical representation 110. By toggling the device-type icons within the panel 140, a user may selectively view one or more types of telepresence devices and disable the display of the other types. Accordingly, a user may filter by telepresence device type.

Additionally, the viewing level 100 may include selectable overlays within an overlay panel 150. The selectable overlays may include, but are not limited to, a population density, a stroke frequency, an adoption rate of a software update, an adoption rate of a firmware update, a frequency of a particular medical condition, a frequency of a particular technical difficulty, an average age of the population, an average age of patients, socioeconomic conditions, an availability of wireless communications, a relative location of medical practitioners, active sessions, a data connection strength, and a relative location of support technicians. The informational overlay may be overlaid on the geographical representation 110 as a heat map, as graphics, as pictures, as icons, as numbers, and/or as text. A user may apply an overlay on geographical representation 110 in order to visualize the relationships between the information conveyed by the overlay, technical data, healthcare networks, and/or telepresence devices.

A lower panel 160 may include additional selectable icons and/or display information about the current session. For example, a reset icon may allow a user to reset or refresh the visualization and management system. A customer networks icon may allow the user to switch from a geographical representation of the relative location of telepresence devices to a geographical representation of the relative location of healthcare facilities and/or healthcare networks, or to a connectivity control panel.

For purposes of this disclosure, the selection of an icon within any of panels 130, 140, 150, and 160 may be considered a transition from the viewing level 100 to a different viewing level. Alternatively, the selection of some of the icons within panels 130, 140, 150, and/or 160 may display additional information, remove displayed information, and/or modify displayed information but remain within the same viewing level. The viewing level 100 illustrated in FIG. 1 may be displayed in a web browser, potentially using one or more plug-ins. Alternatively, the various viewing levels may be displayed and/or controlled in a stand-alone application or in any other suitable computing environment.

Figure 2:
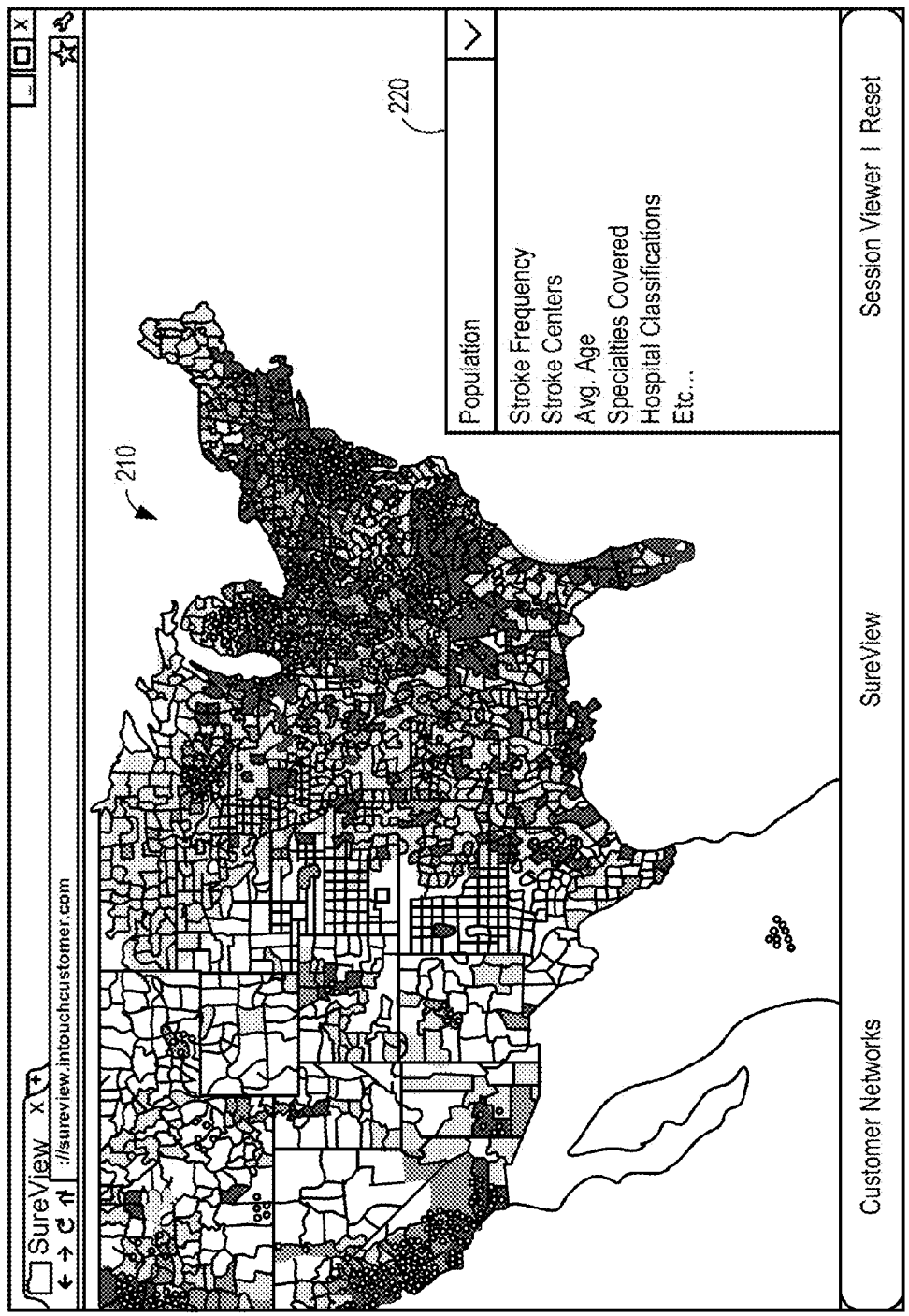
FIG. 2 illustrates a viewing level of a geographical representation of the United States with a population density overlay.

FIG. 2 illustrates a viewing level 200 with a narrower field of view showing a heat map overlaid on a geographical representation 210. The illustrated geographical representation 210 includes the continental United States. As illustrated, an overlay panel 220 may include various informational overlays that may be applied to the geographical representation 210. The overlays may be applied in any of a wide variety of manners, such as by applying a corresponding heat map, graphics, pictures, icons, numbers, and/or text. In the illustrated embodiment, the white dots on the geographical representation 210 may represent available telepresence devices.

The heat map overlay may correspond to a population density. Accordingly, it may be useful (e.g., to assess need or sales opportunities) to compare the population density across the continental United States to the location of available/existing telepresence devices. For instance, in the illustrated example, the population density near the border of Illinois and Iowa is relative high, and yet there is no telepresence device nearby. Accordingly, a sales opportunity or need may exist in that region.

Figure 3:
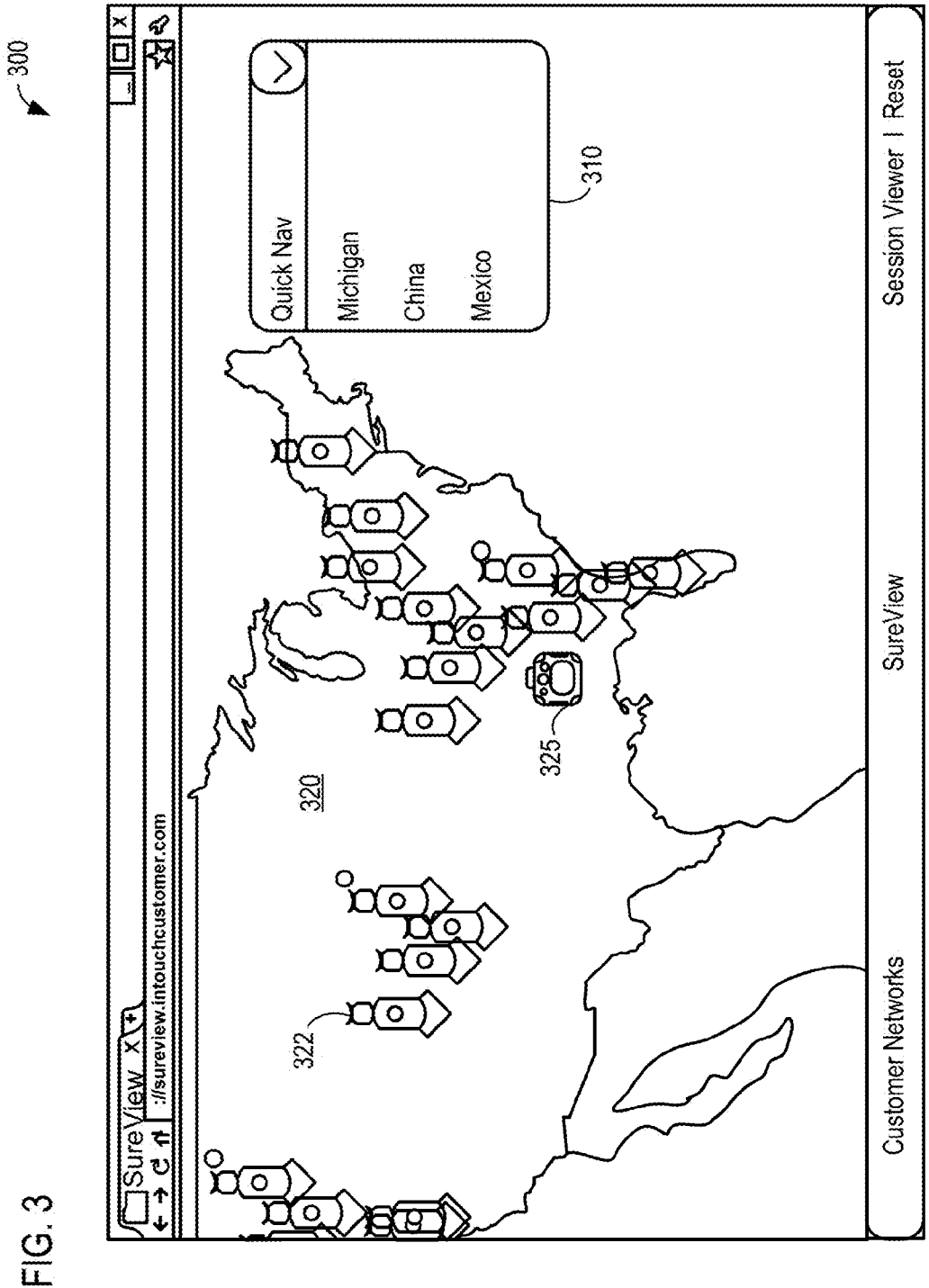
FIG. 3 illustrates a shortcut menu configured to allow for direct navigation to various locations within a geographical representation.

FIG. 3 illustrates a "Quick Nav" shortcut menu 310 configured to allow for direct navigation to a location within the geographical representation 320. The Quick Nav menu 310 may be customized and/or include various default locations. Any number of selectable locations may be included in the shortcut menu 310. Selecting a location within the shortcut menu 310 may pan, rotate, tilt, and/or zoom the window in order to frame the selected geographical location. The telepresence devices and/or healthcare facilities within the framed geographical representation 320 may be displayed as icons resembling corresponding types of telepresence devices and/or healthcare facilities. Alternatively, other symbols, icons, coloring, numbers, text, or markings may be utilized to display the relative location of various telepresence devices and/or healthcare facilities within the displayed geographical boundaries. In the illustrated embodiment, robotically controlled telepresence devices are illustrated with robot icon 322, and mobile telepresence units are illustrated with an icon 325 resembling the device type.

Figure 4B:
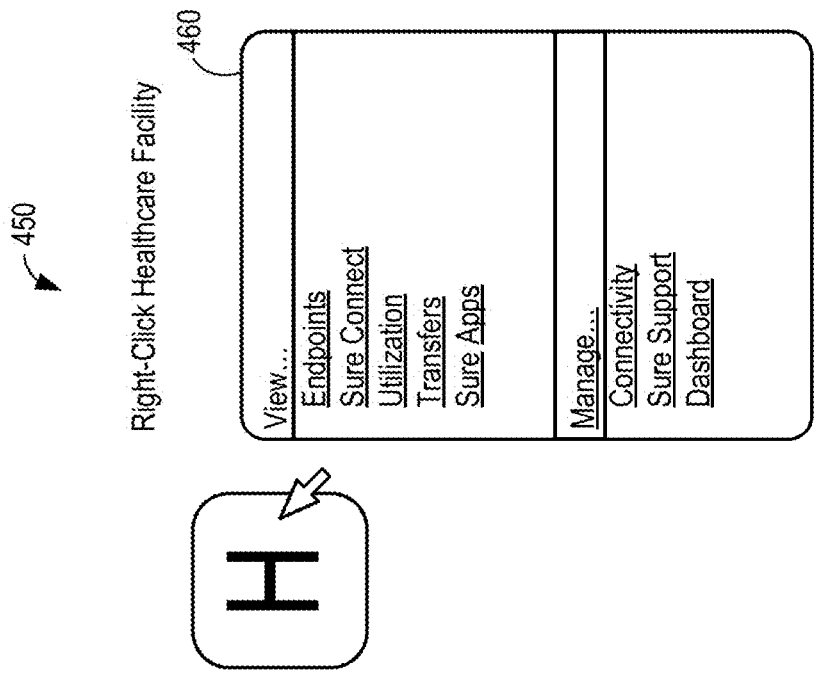
FIGS. 4A and 4B illustrate context-based detail request menus providing access to specific details based on the type of telepresence device and/or type of healthcare facility.
Figure 4A:
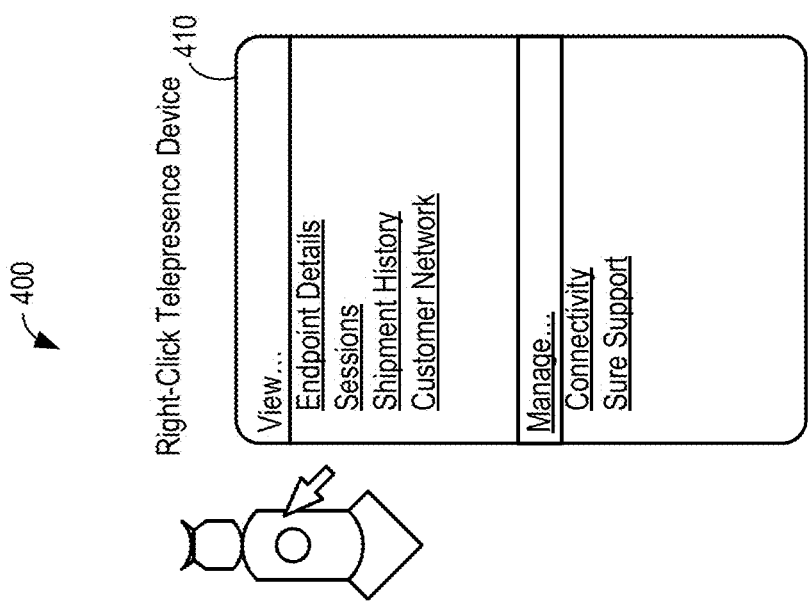

FIGS. 4A and 4B illustrate context-based detail request menus 400 and 450 providing access to specific details based on the type of telepresence device and/or type of healthcare facility. The detailed information, titles, names, and icons used in menus 400 and 450 may be modified or adapted for a particular application or need. As illustrated in FIG. 4A, by right-clicking (or through the use of another secondary selection method) on the robot icon, a user may select various viewing details or management details in panel 410. Detail requests may include information associated with telepresence devices, communication sessions, shipment history, and available networks. Additionally, a user may select various management details, such as connectivity and support. Different types of telepresence devices may include different detail selection options for viewing and/or managing. Moreover, the identity of the user may modify which selectable detail requests are available. For example, an administrator of a telepresence device may have more access than a low-level healthcare practitioner.

As illustrated in FIG. 4B, when a healthcare facility icon is right-clicked, a different detail request panel 460 may be displayed. The selectable detail requests within panel 460 may be based on the identity of the user, a characteristic of the user, the type of healthcare facility, and/or the types of available telepresence devices associated with the healthcare facility. As illustrated, a user may select to view additional details associated with endpoints (telepresence devices) associated with the healthcare facility, connection rules, utilization statistics of telepresence devices, transfer statistics, and other interfacing applications. Additionally, the user may select to manage details such as connectivity, support, and/or a dashboard of other informational details.

Hovering a mouse over a telepresence device icon and/or a healthcare facility icon (a mouse-over) may display one or more details about the specific device/facility. For example, a mouse-over may display the serial number of a telepresence device and the hospital with which it is associated. Additional information may be displayed via a mouse-over and/or by selecting the icon representing the device/facility.

Any of the selectable icons, panels, and/or options may be accessible in any of the viewing levels described herein. Specifically, the viewing level requests via navigation panels and/or shortcut menus (illustrated in FIGS. 1 and 3), the available overlays (illustrated in FIG. 2), and the detail request panels (illustrated in FIGS. 4A and 4B) may be available in the viewing level illustrated in FIG. 1. The exact depictions of icons, panels, geographical representations, and other specific details illustrated and/or described in conjunction with the figures are merely exemplary and may be modified, augmented, replaced, and/or eliminated for a particular application.

Figure 5:
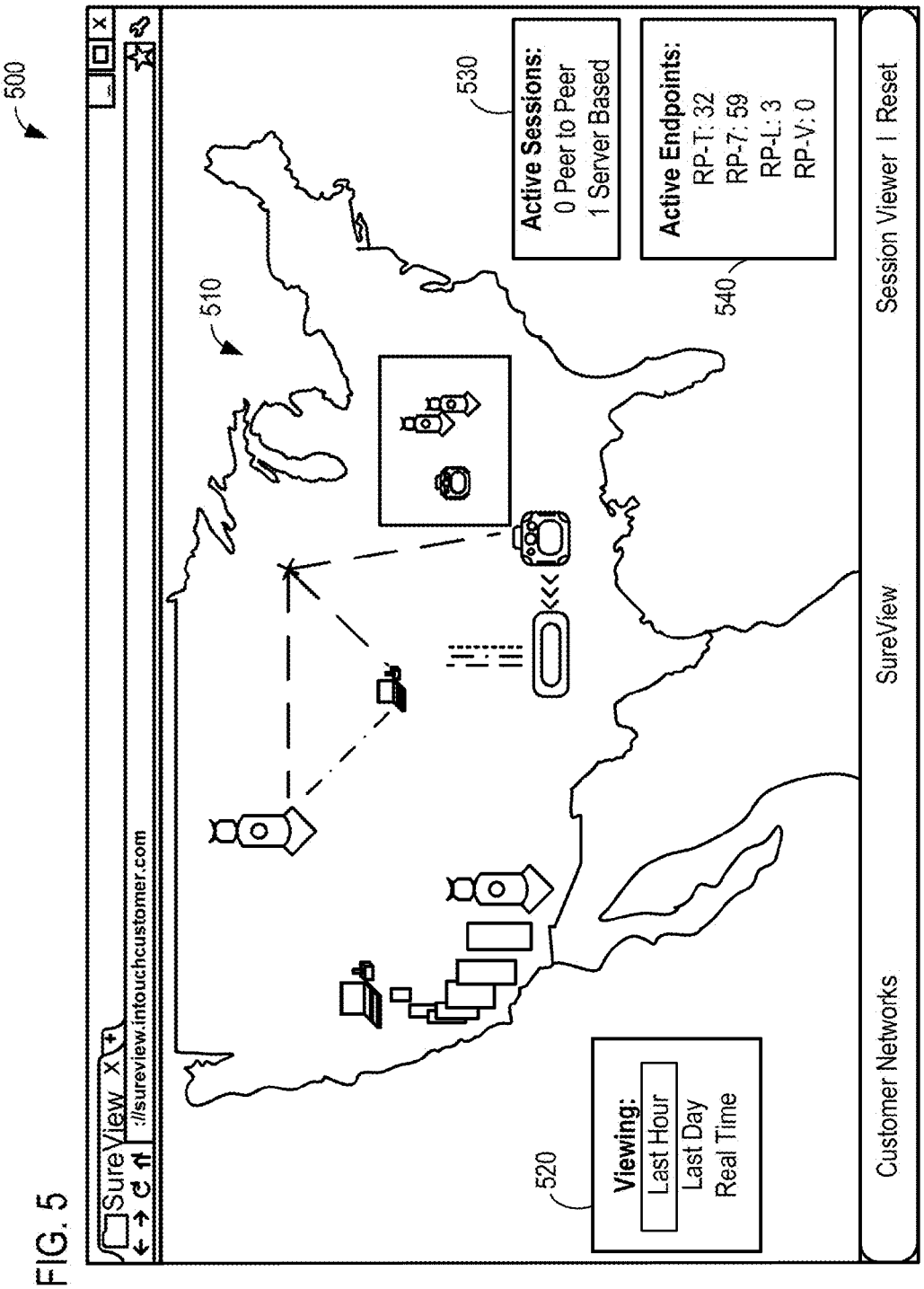
FIG. 5 illustrates a viewing level including a session viewer for monitoring sessions and telepresence devices during a selected time period.

FIG. 5 illustrates a viewing level 500 including a session viewer for visualizing and/or managing sessions and telepresence devices during a selected time period. The session viewer viewing level 500 may allow a user to visualize data relating to specific remote telepresence sessions on a geographic representation 510. The visualization may include a set of lines or arcs representing the connections. As illustrated, a time period may be selected in panel 520, the total number of active sessions may be illustrated in the active session panel 530, and the active telepresence devices (endpoints) may be illustrated in panel 540. Icons representing various telepresence devices, healthcare facilities, and/or communication connections may be displayed on the geographical representation 510, as illustrated in FIG. 5.

In various embodiments, visual attributes and/or text associated with the communication connections may be indicative of a telepresence session's quality, control station used, servers used, and/or other session data. For example, the visual appearance of a communication connection may be modified based on the session's quality, the control station, which server was used to negotiate the connection, the endpoint, the type of session (peer-to-peer or server-based), and/or other session data. A single session, a set of sessions from multiple endpoint and control station pairs at a single point in time, and/or a set of multiple sessions over a time span specified by the user may also be provided in this or another viewing level.

In various embodiments, a viewing level including a session viewer as illustrated in FIG. 5 may allow a user to view the number of active sessions, a list of active telepresence devices, and filtering options to limit the types of devices displayed, the connection types, the server types, the time period, and/or other attributes of telepresence sessions. In some cases, a user may view session data associated with a particular mobile telepresence unit. The visualization and management system may display a geographical representation bounded by a travel area of the mobile telepresence unit.

Figure 6:
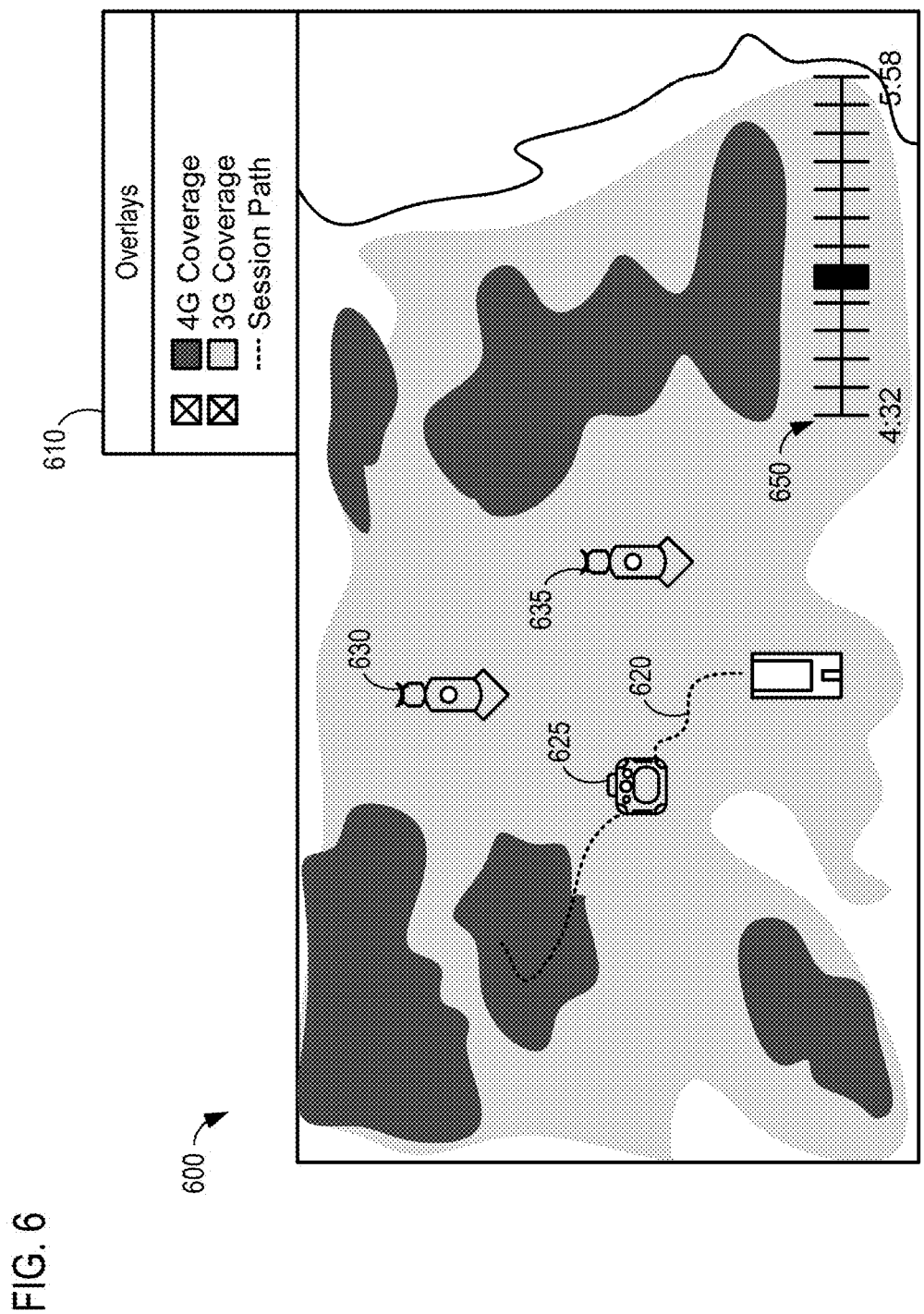
FIG. 6 illustrates a detailed session viewer for monitoring a location of a telepresence device at various time periods on a geographical representation, the geographical representation including an overlay of wireless communication availability.

As illustrated in FIG. 6, various overlays may be used in conjunction with the session viewer viewing level in order to provide additional information about a particular telepresence session. A viewing level 600 may include a route 620 traveled by a mobile telepresence device 625 over a given time period. The viewing level 600 may also include robot telepresence devices 630 and 635 with which the mobile telepresence device 625 communicated. The relative location of the mobile telepresence device 625 may move along the route 620 as the time is moved along the timeline 650 from 4:32 to 5:58 (corresponding to the beginning and end of one or more telepresence sessions).

An overlay, such as 3G and 4G cellular data availability, may be selected from panel 610 and overlaid on the geographical representation of the viewing level 600 in order to provide additional information to the user. The user may diagnose communication problems and/or improve the overall telepresence session experience using various informational overlays. Such a viewing level may be particularly useful for visualizing and/or managing the use of mobile telepresence units transported in ambulances and/or used remotely by healthcare practitioners (e.g., while at home or on vacation). For example, while monitoring a number of active sessions in a session viewer as illustrated in FIG. 5, a user may see an indication of a connection problem associated with a mobile telepresence device. In response, the user may open a session viewer associated with the mobile telepresence device, as illustrated in FIG. 6, and chose to overlay 3G and/or 4G cellular data availability to investigate and discover possible causes of the connection problem.

Figure 7A:
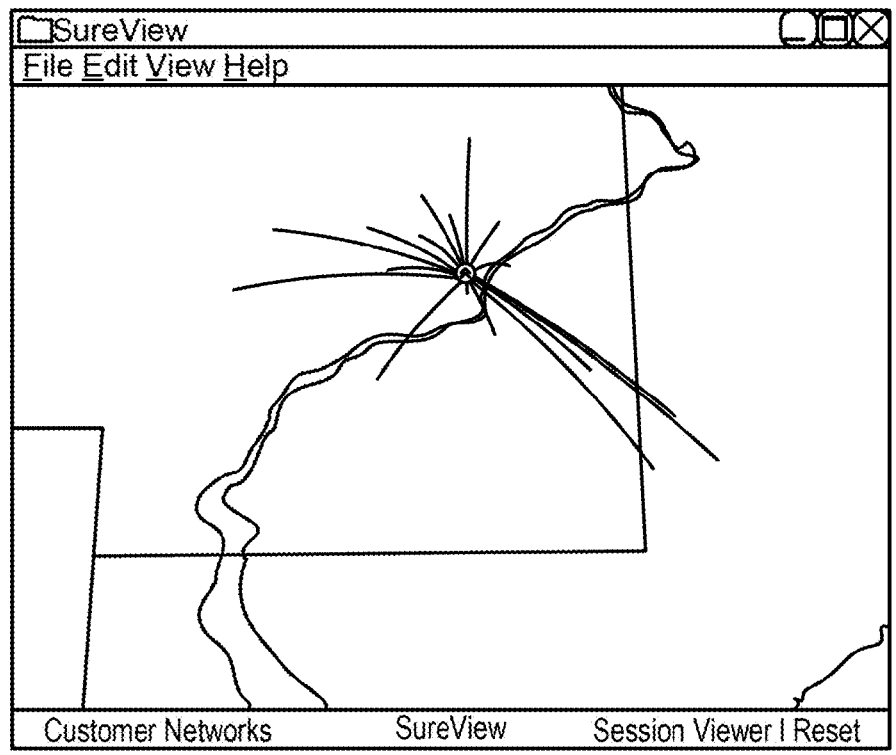
FIGS. 7A and 7B illustrate viewing levels including the location and interconnections of medical facilities in a healthcare network on a geographical representation.

As described in conjunction with FIG. 1, a user may select a viewing level that displays the relative location of at least one healthcare facility and its relationships to other healthcare facilities on a geographical representation. FIG. 7A illustrates a hub healthcare facility, such as a hub hospital, and its relationships with other healthcare facilities as arcs extending from the hub healthcare facility to other related healthcare facilities on a geographical representation. Transitioning to the viewing level 700 may initially remove all telepresence device icons and display a new set of icons representing each customer organization. Different icons may be used to represent each type of healthcare facility and/or the capabilities of each healthcare facility. Additionally, different icons may be used to represent various classes of customers, such as hospitals, clinics, corporate headquarters, partner hospitals, and others. Similar to the description above, hovering over a customer icon may display the organization's name and/or some additional information. Clicking on a customer icon may display all the telepresence devices and/or hospitals associated with the customer's network. Animated arcs representing the current connectivity paths may extend from the customer hub or headquarters to the locations of current telepresence devices.

Figure 7B:
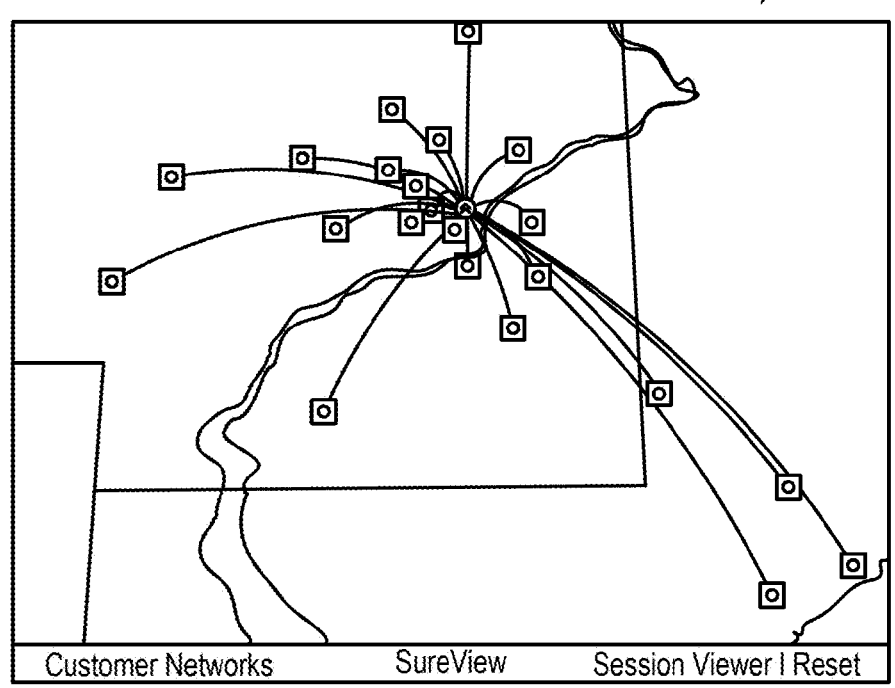

Additional details about arc connections and/or the hub hospital may be made available to a user by selecting or mousing over the icons. FIG. 7B illustrates a viewing level 750 including the location and interconnections of various healthcare facilities in a healthcare network on a geographical representation. Again, context-sensitive detail requests may be made by mousing over the healthcare facilities and/or the connections therebetween.

Additional viewing levels may include menus, icons, and/or other information for visualizing and/or managing the connectivity between various telepresence devices, healthcare practitioners, healthcare facilities, and/or healthcare networks. Additionally, details regarding how and when patients are transferred between various healthcare facilities may be presented as numerical values, as statistics, as graphs, and/or geographically on a geographical representation. In some embodiments, specific viewing levels may be available that display details associated with the shipment history of particular devices and/or software/firmware updates associated with one or more telepresence devices.

For example, a viewing level may include the shipment history of a telepresence device with respect to a timeline. The location of the telepresence device may be visualized at each point during the shipment process. Such a viewing level may allow for the optimization of transportation and shipping of telepresence devices. A viewing level may also be configured to illustrate the progress of an automatic software update from release time to some threshold of acceptance among the telepresence devices in a particular geographical area. For example, a software update is generally released to the entire fleet at a certain time and date. A telepresence device may be automatically updated when it connects to the network. The threshold of acceptance may be when 95% of all telepresence devices have reported that the new update has been installed. The viewing level may provide for the visualization of a software update on a geographical representation. For example, all telepresence devices may initially start with a red circle in their icon to show they have not accepted the update. As the user advances a time bar forward from the release date, the telepresence device icons may change color to show the status of a software update process. This might be from red (not installed) to yellow (downloading from a server) to green (installed). Accordingly, a user may gauge the effectiveness of an automatic software update system. This visualization tool may allow a user to easily identify areas, or specific telepresence devices, where the update process failed or encountered problems.

Figure 8:
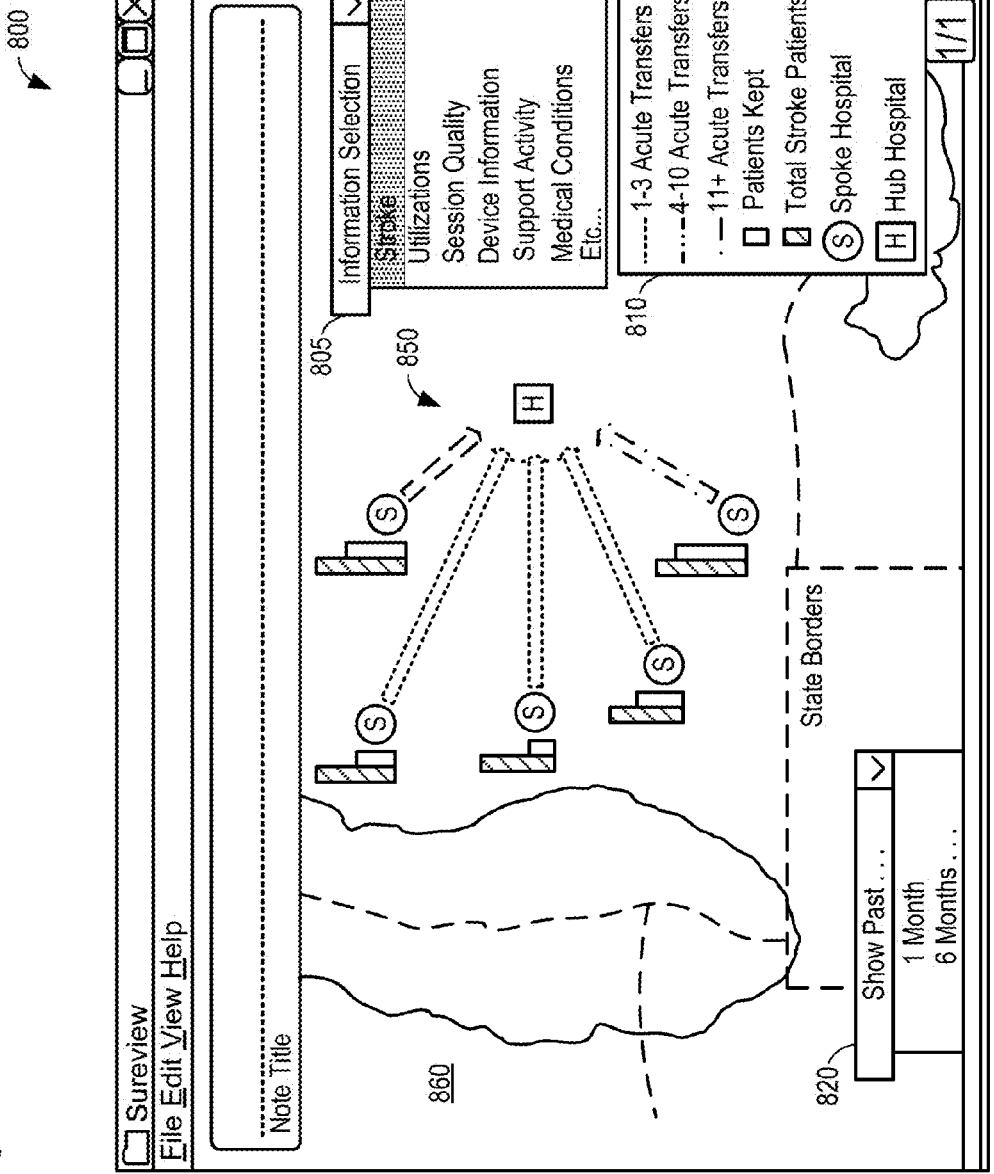
FIG. 8 illustrates a viewing level providing stroke information associated with a healthcare network on a geographical representation.

As illustrated in FIG. 8, a viewing level 800 may display information associated with a healthcare network 850 on a geographical representation 860. A timeline filter may be provided in a panel 820. Viewing level 800 may include an information selection panel 805. Viewing level 800 allows information 805 associated with multiple healthcare facilities 810 and/or telepresence devices to be visually presented in conjunction with a geographical representation 860. A user may select between a variety of informational overlays, graphs, informational tags, icons, text, numbers, connection lines, and/or colors to visually convey information related to healthcare facilities and/or telepresence devices. According to various embodiments, a user may graphically compare data among spoke healthcare facilities or between spoke healthcare facilities and a hub healthcare facility (see key 810) on the geographical representation 860.

In the illustrated embodiment, stroke information has been selected in the information selection panel 805. Accordingly, a user may view the number of patients who were the subject of a stroke consultation made by a healthcare practitioner in a hub healthcare facility using telepresence devices. A user may view the number of such patients who were determined fit to stay in the rural (spoke) healthcare facilities, and those who were transferred to the more capable hub healthcare facility. Such a viewing level may allow for a visualization of the effectiveness and results of consultations via telepresence devices.

The viewing level 800 may allow a user to visualize the value a telepresence system is bringing to a customer's hub hospital and spoke hospitals in terms of patients kept and acute cases transferred. For example, a rural hospital's administrator may visualize the number of patients who were subject to a telepresence consultation performed by a specialist based in a hub hospital. The rural healthcare facility may have a small graph beside it indicating the number of patients kept versus the total number of stroke patients admitted in the selected time period. The healthcare facility may also have an arrow configured with a width corresponding to the relative number of patients transferred from the spoke healthcare facility to the hub healthcare facility. Accordingly, the rural hospital administrator (and the hub hospital administrator) may visualize the benefits of the telepresence devices and telepresence network.

The user may select a different information set from information selection panel 805 in order to visualize data relating to a particular facility or device, or visually compare data between and/or among various spoke and hub healthcare facilities 810 on the geographical representation 860. Additionally, information directly related to the telepresence devices may be selected within information selection panel 805, in order for a user to visually compare the status of telepresence devices between spoke healthcare facilities 810 on the geographical representation 860. Information sets selectable via information selection panel 805 may include, but are not limited to, information related to medical condition, such as stroke or heart attack, utilization rates, session quality information, telepresence device information, support activity, battery levels, last reported time, active session, workflow metrics, available telepresence devices, trained specialists, financial information, subscription information, and/or other information associated with telepresence devices, telepresence networks, healthcare facilities, and/or healthcare networks.

Figure 9:
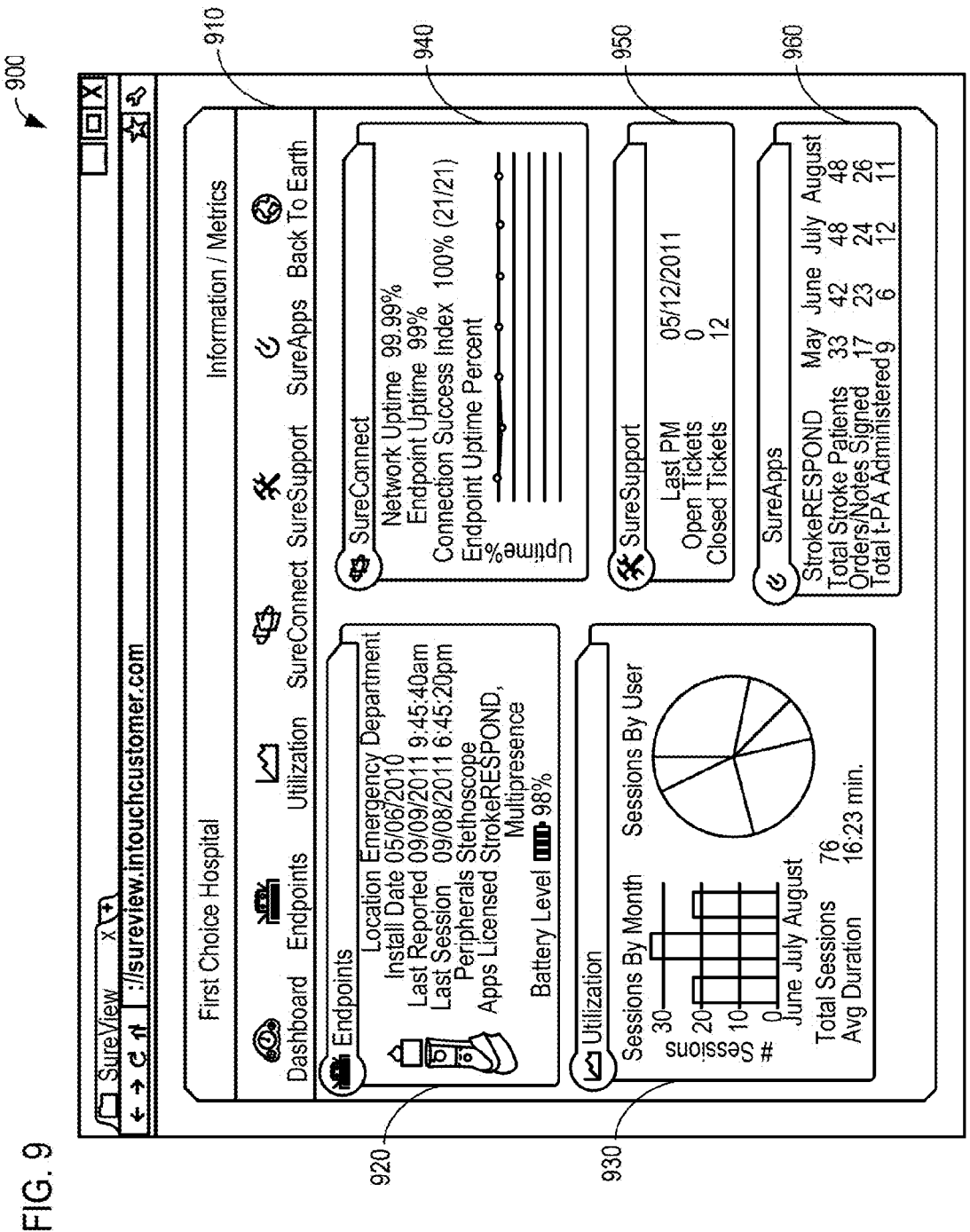
FIG. 9 illustrates a viewing level including a dashboard of detailed information associated with one or more telepresence devices.

FIG. 9 illustrates a viewing level 900 including a dashboard of detailed information 920, 930, 940, 950, and 960 associated with one or more telepresence devices. The displayed details may include various numerical information, charts, and/or graphs. The information displayed in the dashboard of information may depend on the types of telepresence devices, the types of healthcare facilities, and/or the identity of the user. A navigation bar 910 may allow the user to navigate between various viewing levels. In the illustrated example, an endpoint panel 920 may include details associated with one or more endpoints (telepresence devices) in a healthcare facility. Endpoint panel 920 may include real-time information associated with a particular telepresence device, including, but not limited to, a serial number, model number, type, name, battery level, connection status, location, date and time last reported, available peripherals, and associated applications.

A utilization panel 930 may display details associated with the remote telepresence sessions for one or more telepresence devices and/or a particular healthcare facility or network. For example, the utilization panel 930 may include details regarding utilization over various time periods, a total utilization time, an average session duration, a duration of a particular session, a start time and end time of a particular session, a Quality of Service (QoS) for one or more sessions, a current available bandwidth, a bandwidth availability with respect to time, a current location of a telepresence device, and historical locations of a telepresence device with respect to time.

Support panel 950 may display information associated with technical support, software updates, firmware updates, hardware updates/replacements, and/or other support issues. Support panel 950 may display a list of personnel responsible for a telepresence device and/or healthcare facility. Historical data regarding support issues may also be available. Automatic and/or manual updates may be applied via support panel 950 as well.

An application panel 960 may provide information associated with applications registered for use with the telepresence device and/or healthcare facility. Information associated with various workflow applications, such as StrokeRESPOND described in U.S. Patent Application 2010/0191375, which application is hereby incorporated by reference in its entirety, may also be displayed or made accessible in application panel 960.

A connection panel 940 may include information associated with network connections and maintenance. For instance, connection panel 940 may display the basic network start and end times and durations of network connectivity. Connection panel 940 may include a graphical representation of network up-time, network down-time, bandwidth availability, bandwidth use, max ping, average ping, packet loss, and/or other information associated with network connectivity between a telepresence device and a healthcare facility. Network information associated with a connection between two healthcare facilities may also be displayed and/or managed.

Connection panel 940 may additionally, or alternatively, display information associated with connection services configured to provide a reliable and robust peer-to-peer and/or server-based connection across a wide range of network types. For instance, the systems and methods described in U.S. Patent Application 2008/0281467, which application is hereby incorporated by reference in its entirety, may be used in conjunction with the presently described systems and methods. Connection panel 940 may also display information associated with automatic bandwidth tests and/or general profiling of a network.

Figure 10:
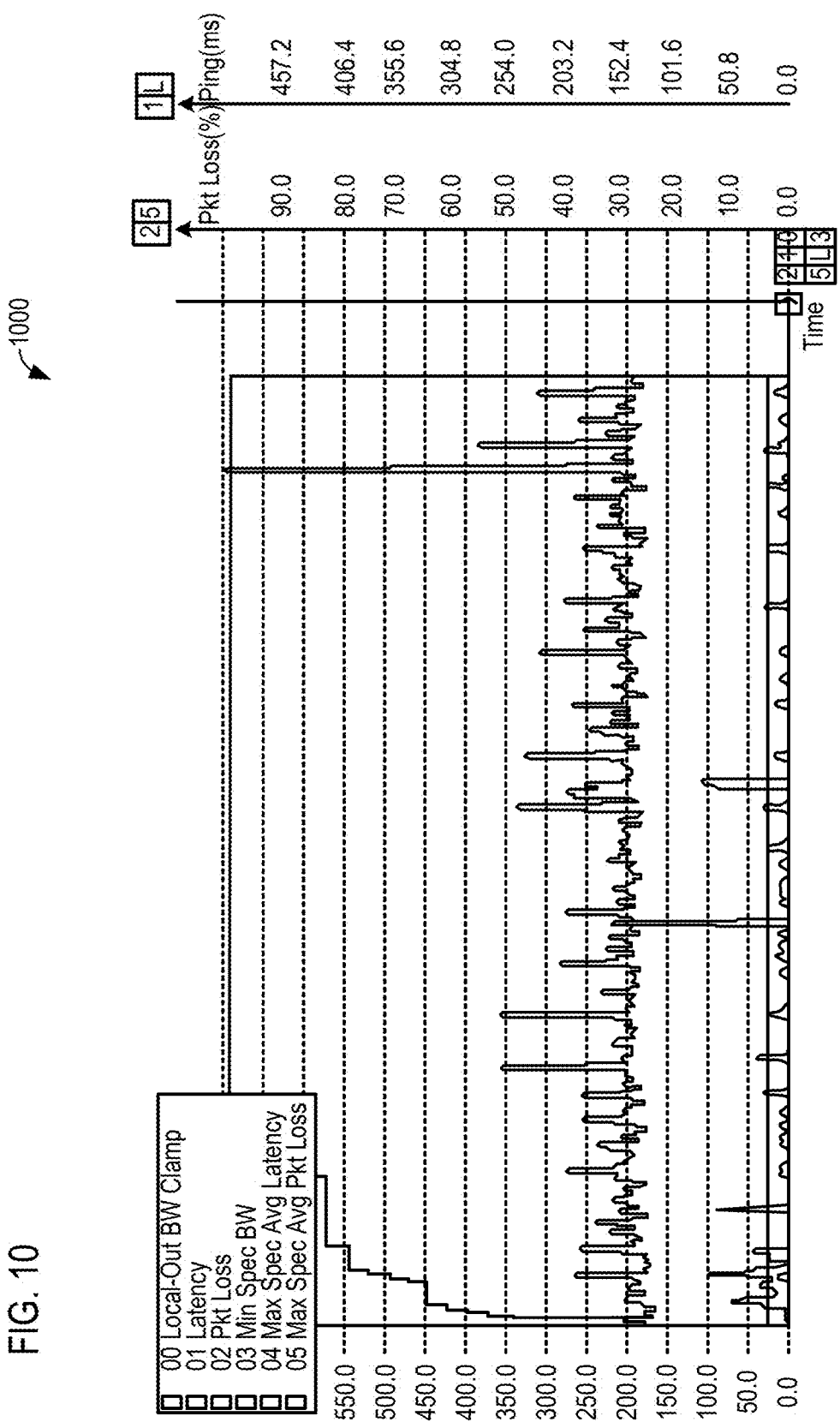
FIG. 10 illustrates a viewing level including session details for a particular telepresence device.

FIG. 10 illustrates a viewing level 1000 displaying the dynamic bandwidth management, latency, and packet loss during various time periods for one or more telepresence devices. Such a viewing level 1000 may be useful for a user to diagnose networking problems and/or improve a telepresence network.

Figure 11:
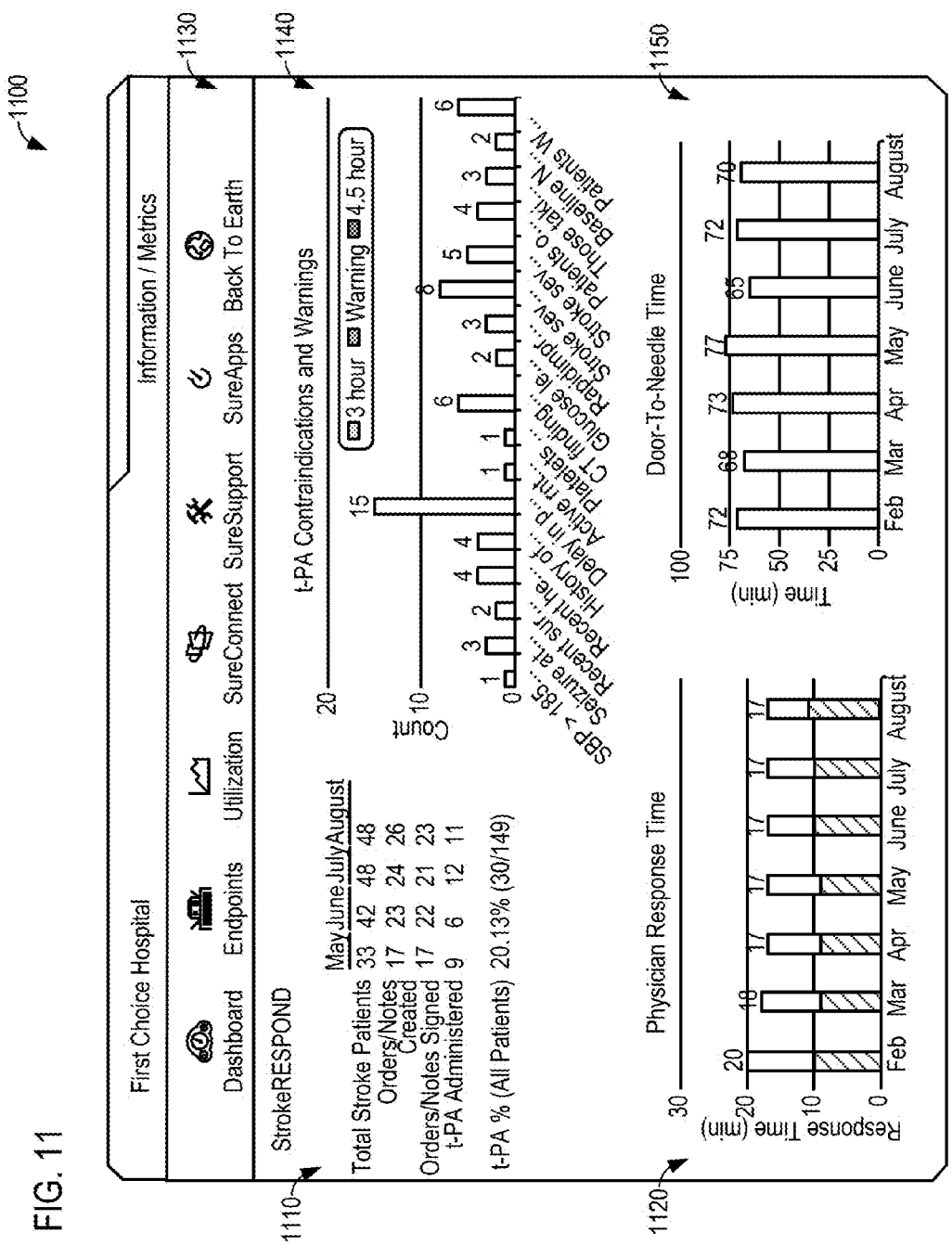
FIG. 11 illustrates a viewing level including stroke information associated with a healthcare network provided via a StrokeRESPOND application.

FIG. 11 illustrates a viewing level 1100 of an application selected via application panel 960 in FIG. 9. The exemplary information panels illustrated in FIG. 11 are associated with the application StrokeRESPOND. Any of a wide variety of application interfaces may be accessible via the visualization and management system described herein. As illustrated, information associated with strokes may be displayed in conjunction with the StrokeRESPOND application. For instance, the display may include a door-to-needle time 1150 corresponding to the amount of time between a patient's arrival at a healthcare facility and the time the patient receives clot-busting medication. The display may also include StrokeRESPOND statistics 1110, physician response times 1120, and/or t-PA contraindications and warning information 1140. A user may navigate to alternative viewing levels and/or return to the previous viewing level via panel 1130.

Figure 12:
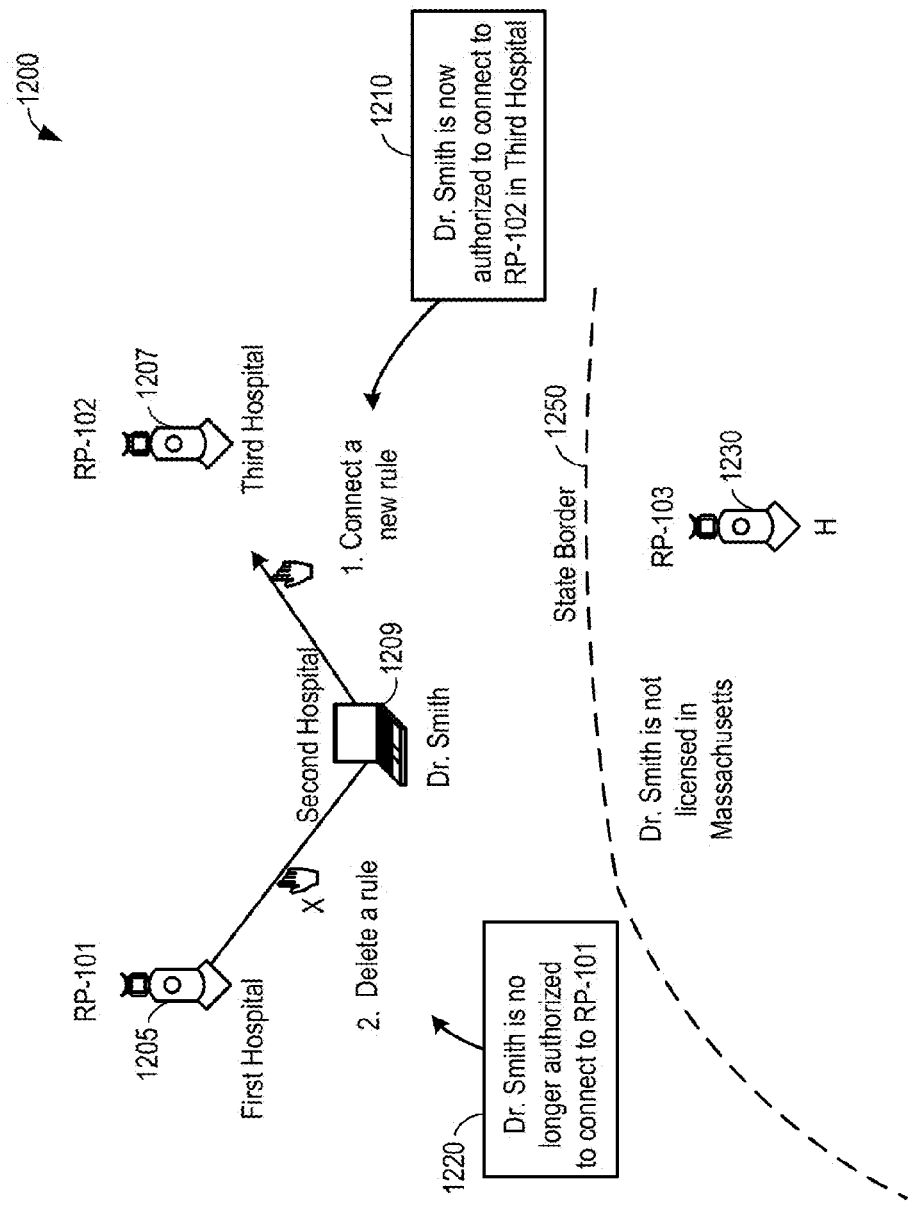
FIG. 12 illustrates a viewing level allowing for the management of connection rules between healthcare practitioners, healthcare facilities, and telepresence devices.

According to various embodiments, a user may select a viewing level 1200 allowing for the management of connection rules between telepresence devices, healthcare facilities, and/or healthcare practitioners, as illustrated in FIG. 12. Connection rules may be managed using any of a wide variety of systems and methods, including those described in U.S Patent Applications 2010/0131102 and 2010/0131103, which applications are hereby incorporated by reference in their entireties.

As illustrated, a control station 1209 may be accessible to a Dr. Smith. An existing connection rule allows Dr. Smith to access telepresence device RP-101 in First Hospital 1205. By deleting this connection rule, at 1220, Dr. Smith will no longer be authorized to connect to RP-101 in First Hospital 1205. By drawing a connection rule between the control station 1209 in Second Hospital and RP-102 in Third Hospital 1207, a new connection rule authorizes Dr. Smith to connect to RP-102 in Third Hospital, at 1210.

The visualization and management system may recognize the state border 1250 and that Dr. Smith is not licensed in Massachusetts. Accordingly, the visualization and management system may prevent a connection rule from authorizing Dr. Smith to access RP-103 in Massachusetts 1230. Similar management methods may be used to manage connection rules between any combination of healthcare practitioners, healthcare facilities, telepresence devices, and/or other users. As illustrated, a user may easily visualize and manage various connection rules using the systems and methods described herein. Specifically, the drag-and-drop methods described above provide for intuitive management of complex connection rules between a large number of healthcare practitioners, healthcare facilities, and/or telepresence devices.

Figure 13:
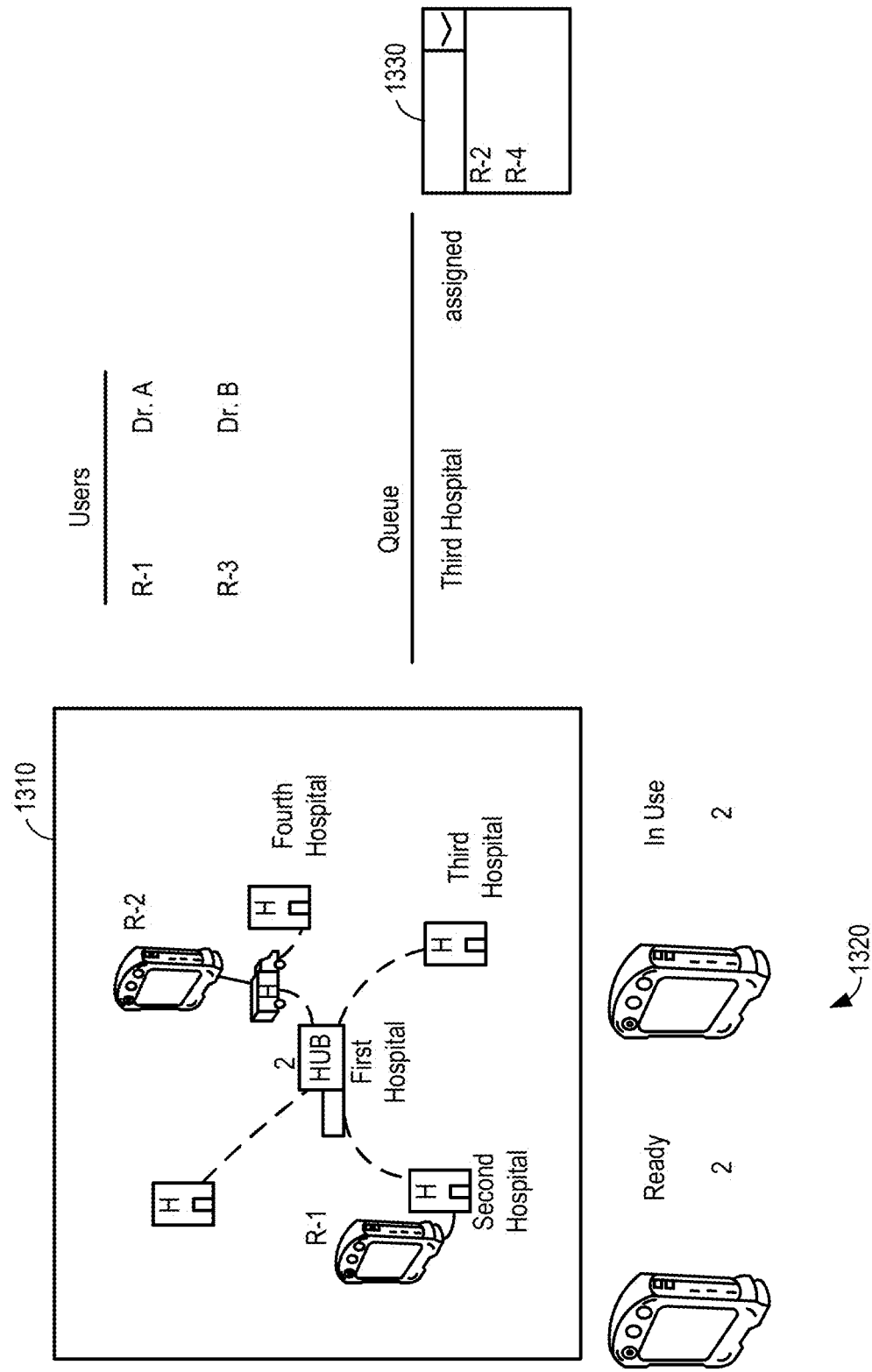
FIG. 13 illustrates a viewing level configured to allow for the management of the usage of the telepresence devices with a geographical visualization tool.

FIG. 13 illustrates another viewing level 1300 accessible to a user. The viewing level 1300 may display the relative location of a number of telepresence devices 1310 and 1320. The viewing level 1300 may include a transfer center interface for managing mobile telepresence units 1310 and 1320. The user may track the geographic location of various mobile telepresence units and determine which units are in use 1310, who is using them, and when they are scheduled to be available. Accordingly, user may manage a queue 1330 of mobile telepresence units.

Figure 14:
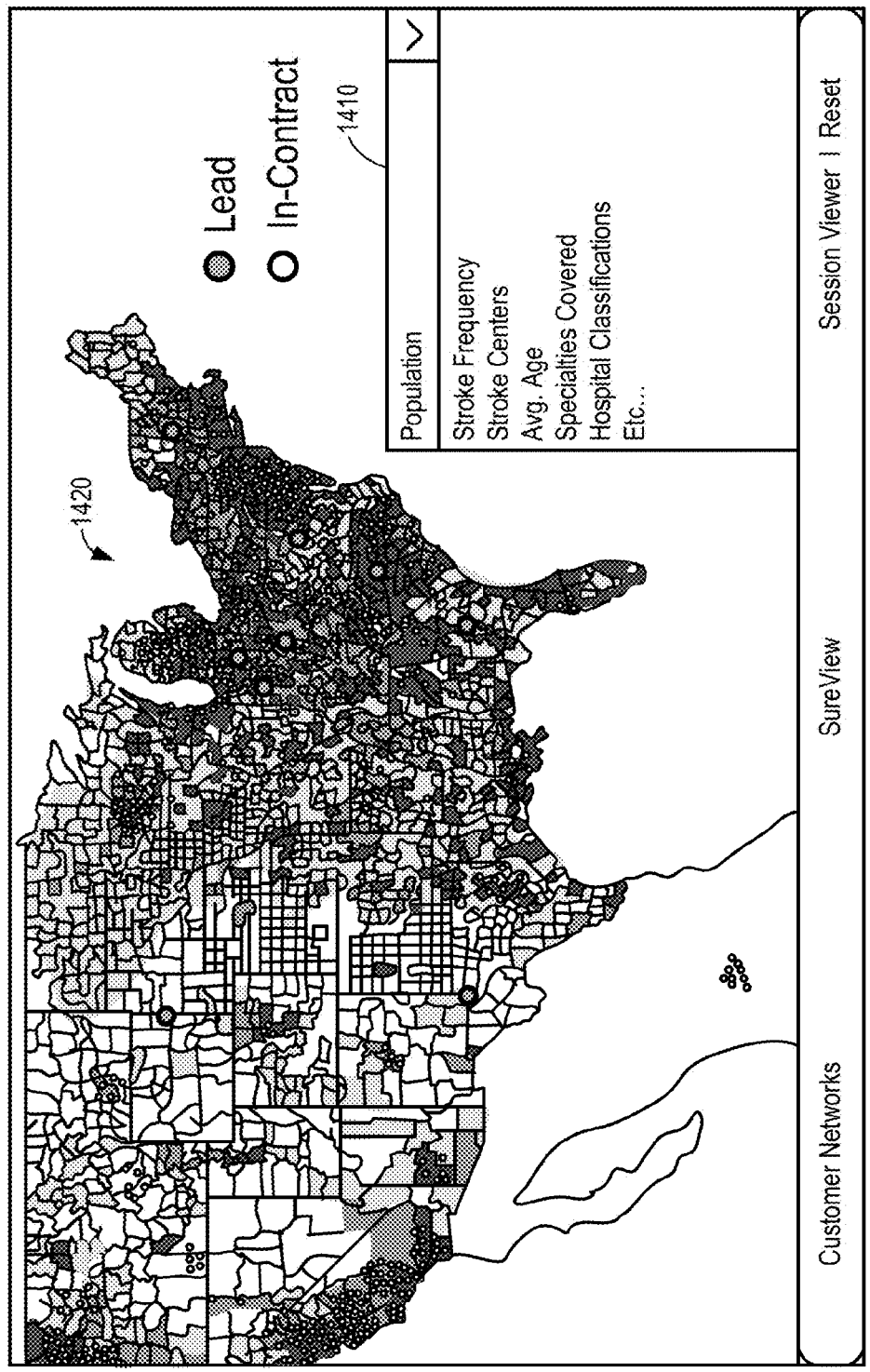
FIG. 14 illustrates a viewing level including a geographical representation of the United States with an overlay of information associated with a potential need for telepresence devices.

FIG. 14 illustrates a viewing level 1400 that may be useful for identifying a need for additional telepresence devices. The illustrated viewing level 1400 may include a geographical representation 1420 of the United States. The geographical representation 1420 may be overlaid with a population density heat map, a stroke frequency heat map, an average age heat map, an availability of a particular medical specialty, hospital classifications, and/or other medical or demographical information. Additionally, the locations of existing telepresence device contracts and/or sales leads may be displayed as white dots on the geographical representation 1420. The overlays may be selectively toggled within overlay panel 1410. A user may utilize the visualization tools to identify needs and/or prospective sales opportunities.

Figure 15:
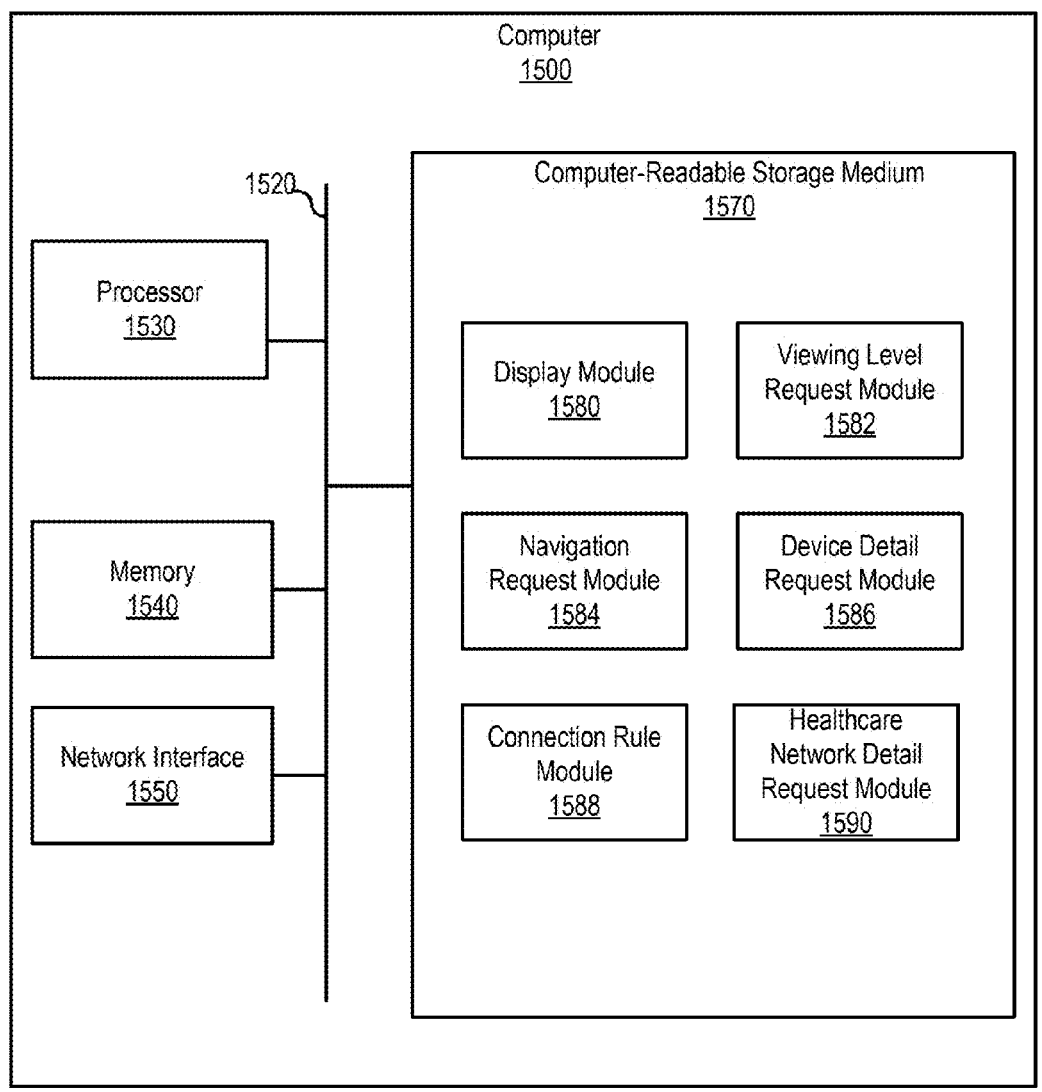
FIG. 15 illustrates a functional block diagram of a computer system including various modules for a telepresence network visualization and management system.

FIG. 15 illustrates a functional block diagram of a computer system 1500 including various modules 1570 for a telepresence network visualization and management system. As illustrated, computer system 1500 may include a processor 1530, memory (such as RAM) 1540, and a network interface 1550 connected via a bus 1520. The bus 1520 may also connect a computer-readable storage medium 1570. The computer-readable storage medium 1570 may include various modules, such as a display module 1580, a viewing level request module 1582, a navigation request module 1584, a device detail request module 1586, a connection rule module 1588, and a healthcare network detail request module 1590. Additional modules may be included, or some modules may be omitted, in order for a computer system to perform any of the server-side or client-side functions of the various systems and methods described herein.

The display module 1580 may be configured to display a viewing level of a telepresence network on a geographical representation. The viewing level request module 1582 may be configured to receive a viewing request to cause the display module 1580 to provide a second viewing level. The navigation request module 1584 may be configured to receive a navigational request to navigate within the geographical representation. The device detail request module 1586 may be configured to receive a detail request to cause the display module 1580 to display a third viewing level, the third viewing level including information associated with one or more telepresence devices. The connection rule module 1588 may be configured to allow for the management of a connection rule governing telepresence devices. The healthcare network detail request module 1590 may be configured to receive a healthcare network detail request to cause the display module 1580 to display a fourth viewing level, the fourth viewing level including information associated with healthcare facilities.

Many changes may be made to the details of the above-described embodiments without departing from the underlying principles and scope of the present disclosure. Accordingly, the scope of the presently described systems and methods should be determined only by the following claims.

What is claimed:

1. A system for managing a telepresence network, comprising:
   a display module configured to display a first viewing level of a telepresence network, the first viewing level comprising a geographical representation of the relative location of a plurality of telepresence devices within the telepresence network;
   a viewing level request module configured to receive a viewing request to cause the display module to provide a second viewing level;
   a navigation module configured to receive a navigational request to navigate within the geographical representation; and
   a device detail request module configured to receive a detail request to cause the display module to display a third viewing level, the third viewing level comprising information associated with at least one of the plurality of telepresence devices, wherein the first viewing level comprises a geographical representation of at least one hub hospital having at least one telepresence device, each hub hospital connected to at least one spoke hospital having at least one telepresence device.

2. The system of claim 1, wherein the first viewing level further comprises a representation of interconnections between a hub telepresence device and at least one endpoint telepresence device.

3. The system of claim 1, wherein in at least one viewing level an information selection module is configured to receive an information request; and wherein information associated with at least one of the plurality of telepresence devices is displayed on the geographical representation corresponding to the information request.

4. The system of claim 3, wherein the information is associated with one of a medical condition, telepresence network utilization information, telepresence session quality information, telepresence device information, support activity, battery levels, currently active session, workflow metrics, available telepresence devices, trained specialists, financial information, and subscription information.

5. The system of claim 1, wherein the viewing level request module is configured to receive a field of view modification request, such that the second viewing level comprises a modified geographical representation of the relative location of the plurality of telepresence devices within the telepresence network.

6. The system of claim 5, wherein the second viewing level comprises a narrower field of view, and wherein in the narrower field of view, additional information associated with at least one of the telepresence devices is displayed.

7. The system of claim 1, wherein each of the plurality of telepresence devices comprises one of a remote telepresence robot, a mobile telepresence unit, and a control station.

8. The system of claim 1, wherein the viewing request received by the viewing level request module comprises a request for an informational overlay to be displayed in conjunction with the geographical representation.

9. The system of claim 8, wherein the informational overlay comprises a population overlay indicating the population density relative to the geographical representation.

10. The system of claim 8, wherein the informational overlay indicates the frequency of strokes relative to the geographical representation.

11. The system of claim 1, wherein the display module is further configured to overlay information associated with an adoption rate of one of a software update and a firmware update applied to at least a portion of the plurality of telepresence devices.

12. The system of claim 11, wherein the overlay of information associated with the adoption rate of one of the software update and the firmware update is displayed using a color overlay.

13. The system of claim 8, wherein the informational overlay is associated with one of a frequency of a medical condition, an average age of the population, an average age of patients, a socioeconomic condition, an availability of wireless data communication, a relative location of a medical professional, and a relative location of a support technician.

14. The system of claim 8, wherein the geographical overlay is overlaid on only a portion of the displayed geographical representation.

15. The system of claim 14, wherein the portion of the displayed geographical representation corresponds to a geographical area serviced by one of a healthcare network, a hospital, a hub hospital, an endpoint hospital, a particular telepresence device, and a particular medical practitioner.

16. The system of claim 1, wherein the first viewing level further comprises a panel of icons, each icon associated with a type of telepresence device.

17. The system of claim 16, wherein each icon is configured to allow the associated type of telepresence device to be toggled between being displayed on the geographical representation and being removed from the geographical representation.

18. The system of claim 1, wherein the first viewing level further comprises at least one shortcut icon, the shortcut icon associated with one of a predetermined viewing level, a predetermined navigation request, and a predetermined detail request.

19. The system of claim 1, wherein receiving the detail request comprises selecting at least one of the plurality of telepresence devices displayed on the geographical representation.

20. The system of claim 19, wherein the third viewing level comprises displaying the information associated with at least one of the plurality of telepresence devices as an overlay of information on the geographical representation.

21. The system of claim 19, wherein displaying the third viewing level comprises displaying the information associated with the at least one of the plurality of telepresence devices in place of the geographical representation of the first viewing level.

22. The system of claim 1, wherein receiving the detail request comprises a mouse-over selection of at least one of the plurality of telepresence devices displayed on the geographical representation.

23. The system of claim 22, wherein the third viewing level comprises displaying the information associated with the at least one of the plurality of telepresence devices as an overlay of information on the geographical representation.

24. The system of claim 1, wherein the information associated with at least one of the plurality of telepresence devices displayed in the third viewing level comprises the number of active sessions associated with the at least one of the plurality of telepresence devices.

25. The system of claim 1, wherein the information associated with at least one of the plurality of telepresence devices displayed in the third viewing level comprises the connection strength associated with the at least one of the plurality of telepresence devices.

26. The system of claim 1, wherein the information associated with at least one of the plurality of telepresence devices displayed in the third viewing level comprises a location of a telepresence device at a selectable time along a timeline.

27. The system of claim 26, wherein the location of the telepresence device at a selectable time along a timeline is displayed relative to a geographical representation including an overlay of an availability of wireless data communication.

28. The system of claim 1, wherein the information associated with at least one of the plurality of telepresence devices displayed in the third viewing level comprises a connection rule of the at least one of the plurality of telepresence devices.

29. The system of claim 28, further comprising a connection rule management module configured to allow for the management of a connection rule of the at least one of the plurality of telepresence devices in the third viewing level.

30. The system of claim 29, wherein the connection rule management module is configured to allow for drag-and-drop connection rule management.

31. The system of claim 1, wherein the information associated with at least one of the plurality of telepresence devices displayed in the third viewing level comprises information pertaining to the shipment process of the at least one of the plurality of telepresence devices.

32. The system of claim 1, wherein the information associated with at least one of the plurality of telepresence devices displayed in the third viewing level comprises information pertaining to one of a software update and a firmware update of the at least one of the plurality of telepresence devices.

33. The system of claim 1, wherein the information associated with at least one of the plurality of telepresence devices displayed in the third viewing level comprises information pertaining to one of a serial number, a model number, a battery level, a location, a date the telepresence device last reported, a time the telepresence device last reported, historical session data, a registered peripheral, a licensed application, a total utilization time, an average session duration, a duration of a particular session, a start time of a particular session, an end time of a particular session, a Quality of Service (OoS) for one or more sessions, a current available bandwidth, and a bandwidth availability with respect to time.

34. The system of claim 1, wherein in the first viewing level an information selection module is configured to receive an information request; and wherein information associated with at least one of the hospitals is displayed on the geographical representation corresponding to the information request.

35. The system of claim 34, wherein the information is associated with one of a medical condition, telepresence network utilization information, telepresence session quality information, telepresence device information, support activity, battery levels, currently active session, workflow metrics, available telepresence devices, trained specialists, financial information, and subscription information.

36. The system of claim 1, further comprising a healthcare network detail request module configured to receive a healthcare network detail request to cause the display module to display a fourth viewing level, the fourth viewing level displaying information associated with the at least one hub hospital and the at least one spoke hospital.

37. The system of claim 36, wherein receiving the healthcare network detail request comprises selecting one of the at least one hub hospital and the at least one spoke hospital.

38. The system of claim 37, wherein the fourth viewing level comprises displaying the information associated with one of the at least one hub hospital and the at least one spoke hospital as an overlay of information on the geographical representation.

39. The system of claim 37, wherein the fourth viewing level comprises displaying the information associated with one of the at least one hub hospital and the at least one spoke hospital in place of the geographical representation of the first viewing level.

40. The system of claim 36, wherein receiving a detail request comprises a mouse-over selection of one of the at least one hub hospital and the at least one spoke hospital.

41. The system of claim 40, wherein the fourth viewing level comprises displaying the information associated with one of the at least one hub hospital and the at least one spoke hospital as an overlay of information on the geographical representation.

42. The system of claim 40, wherein the information associated with one of the at least one hub hospital and the at least one spoke hospital displayed in the fourth viewing level comprises one of a number of active sessions, a number of active telepresence devices, a connection strength of telepresence devices, a connection between two or more telepresence devices, a location of a telepresence device, information from a StrokeRESPOND application, a door-to-needle time, a door-to-balloon time, a t-PA contraindication, a t-PA warning, a medical practitioner response time, and a call center response time.

43. The system of claim 42, wherein the information associated with one of the at least one hub hospital and the at least one spoke hospital displayed in the fourth viewing level is associated with one of a particular hospital, a network of hospitals, a medical practitioner, a telepresence device, a patient, and a geographical area.

44. A method for managing a telepresence network, comprising:
displaying a first viewing level of a telepresence network, the first viewing level comprising a geographical representation of the relative location of a plurality of telepresence devices within the telepresence network;

displaying a second viewing level in response to receiving a viewing request for the second viewing level;

navigating within the geographical representation in response to receiving a navigational request; and displaying a third viewing level in response to receiving a detail request, the third viewing level comprising information associated with at least one of the plurality of telepresence devices, wherein the first viewing level comprises a geographical representation of at least one hub hospital having at least one telepresence device, each hub hospital connected to at least one spoke hospital having at least one telepresence device.

45. A computer program product, comprising a non-transitory computer-readable medium having executable computer program code, the computer program code configured to cause a computer to:

display a first viewing level of a telepresence network, the first viewing level comprising a geographical representation of the relative location of a plurality of telepresence devices within the telepresence network;

receive a viewing request to cause the display module to provide a second viewing level;

receive a navigational request to navigate within the geographical representation; and receive a detail request to cause the display module to display a third viewing level, the third viewing level comprising information associated with at least one of the plurality of telepresence devices, wherein the first viewing level comprises a geographical representation of at least one hub hospital having at least one telepresence device, each hub hospital connected to at least one spoke hospital having at least one telepresence device.

* * * * *